United States Patent
Castro Pineiro et al.

(10) Patent No.: US 7,265,110 B2
(45) Date of Patent: *Sep. 4, 2007

(54) TETRAHYDROPYRAN DERIVATIVES AND THEIR USE AS THERAPEUTIC AGENTS

(75) Inventors: Jose Luis Castro Pineiro, Bishops Stortford (GB); Duncan Edward Shaw, Bishops Stortford (GB); Brian John Williams, Great Dunmow (GB)

(73) Assignee: Merck Sharp & Dohme Limited, Hertfordshire (GB)

( * ) Notice: Subject to any disclaimer, the term of this patent is extended or adjusted under 35 U.S.C. 154(b) by 324 days.

This patent is subject to a terminal disclaimer.

(21) Appl. No.: 10/488,842

(22) PCT Filed: Sep. 6, 2002

(86) PCT No.: PCT/GB02/04085

§ 371 (c)(1),
(2), (4) Date: Mar. 4, 2004

(87) PCT Pub. No.: WO03/022839

PCT Pub. Date: Mar. 20, 2003

(65) Prior Publication Data

US 2004/0254184 A1    Dec. 16, 2004

(30) Foreign Application Priority Data

Sep. 10, 2001    (GB) ................... 0121874.2

(51) Int. Cl.
| | | |
|---|---|---|
| A61K 31/351 | (2006.01) | |
| A61K 31/451 | (2006.01) | |
| A61K 31/5377 | (2006.01) | |
| C07D 265/30 | (2006.01) | |
| C07D 295/00 | (2006.01) | |

(52) U.S. Cl. .................. 514/231.5; 514/326; 514/460; 544/107; 546/207; 548/407; 548/529; 549/416

(58) Field of Classification Search ............ 514/231.5, 514/326, 460; 544/107; 546/207; 549/416; 548/407, 529
See application file for complete search history.

(56) References Cited

U.S. PATENT DOCUMENTS

| | | |
|---|---|---|
| 6,071,927 A | 6/2000 | Baker et al. |
| 2002/0035132 A1 | 3/2002 | Williams et al. |

FOREIGN PATENT DOCUMENTS

| | | |
|---|---|---|
| WO | WO 0056727 A | 9/2000 |
| WO | WO03/022839 A1 | 3/2003 |

*Primary Examiner*—Taofiq Solola
(74) *Attorney, Agent, or Firm*—Curtis C. Panzer; Patricia A. Shatynski

(57) ABSTRACT

The present invention relates compounds of the formula (I); wherein $R^1$, $R^2$, $R^3$, $R^4$, $R^5$, $R^6$, $R^7$, $R^8$, and $R^{10}$ represent a variety of substituents; A represents $NR^9$ or O; B represents a bond, $CH_2$, $NR^9$ or O, wherein one or both hydrogen atoms in said $CH_2$ moiety may be replaced with one or both of $R^7$ and $R^8$, or alternatively, one of the hydrogen atoms in said $CH_2$ moiety together with a hydrogen atom from an adjacent carbon are replaced by a double bond; with the proviso that when A is O, then B is $NR^9$; n is zero, 1 or 2; and pharmaceutically acceptable salts thereof. The compounds are of particular use in the treatment or prevention of depression, anxiety, pain, inflammation, migaine, emesis or postherpetic neuralgia

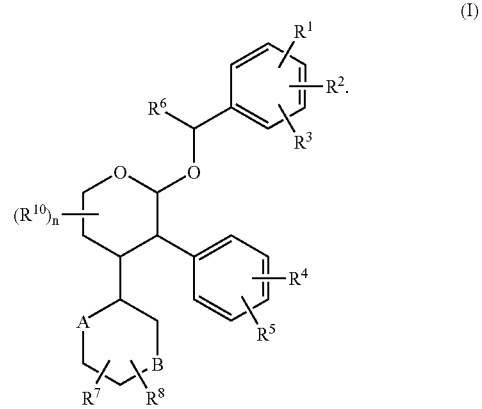

20 Claims, No Drawings

TETRAHYDROPYRAN DERIVATIVES AND THEIR USE AS THERAPEUTIC AGENTS

CROSS REFERENCE TO RELATED APPLICATIONS

This application is a U.S. National Phase application under 35 U.S.C. § 371 of PCT Application No. PCT/GB02/0485, filed Sep. 6, 2002, which claims priority under 35 U.S.C. § 119 from GB Application No. 0121874.2, filed Sep. 10, 2001.

This invention relates to a class of tetrahydropyran compounds which are useful as tachykinin antagonists. More particularly, the compounds of the invention are useful as neurokinin 1 (NK-1) receptor antagonists.

The present invention provides compounds of the formula (I):

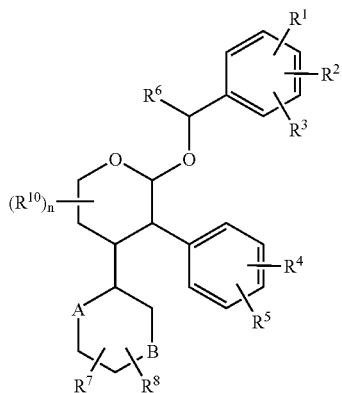

wherein

A represents $NR^9$ or O;

B represents a bond, $CH_2$, $NR^9$ or O, wherein one or both hydrogen atoms in said $CH_2$ moiety may be replaced with one or both of $R^7$ and $R^8$, or alternatively, one of the hydrogen atoms in said $CH_2$ moiety together with a hydrogen atom from an adjacent carbon are replaced by a double bond;

with the proviso that when A is O, then B is $NR^9$;

$R^1$ is hydrogen, halogen, $C_{1-6}$alkyl, $C_{1-6}$alkoxy, fluoro$C_{1-6}$alkyl, fluoro$C_{1-6}$alkoxy, $C_{3-7}$cycloalkyl, $C_{3-7}$cycloalkyl$C_{1-4}$alkyl, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, fluoro$C_{1-6}$alkyl or $C_{1-6}$alkoxy substituted by $C_{1-4}$alkoxy;

$R^3$ is hydrogen, halogen or fluoro$C_{1-6}$alkyl;

$R^4$ is hydrogen, halogen, $C_{1-6}$alkyl, $C_{1-6}$alkoxy, fluoro$C_{1-6}$alkyl, fluoro$C_{1-6}$alkoxy, hydroxy, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, fluoro$C_{1-6}$alkyl or $C_{1-6}$alkoxy substituted by $C_{1-4}$alkoxy;

$R^6$ represents hydrogen or a $C_{1-4}$alkyl group optionally substituted by a hydroxy group;

$R^7$ and $R^8$ each independently represent hydrogen, hydroxy, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group, where $R^e$ is hydrogen, methyl ethyl or benzyl;

or, when they are attached to the same carbon atom, $R^7$ and $R^8$ may together represent =O, $=CHCO_2R^a$, $-O(CH_2)_mO-$, $-CH_2O(CH_2)_p-$, $-CH_2OCH_2C(O)-$, $-CH_2OCH_2CH(OH)-$, $-CH_2OCH_2C(CH_3)_2-$, $-CH_2OC(CH_3)_2CH_2-$, $-C(CH_3)_2OCH_2CH_2-$, $-CH_2C(O)OCH_2-$, $-OC(O)CH_2CH_2-$, $-C(O)OCH_2CH_2-$, $-C(O)OC(CH_3)_2CH_2-$, $-C(O)OCH_2C(CH_3)_2-$, $-OCH_2(CH_2)_p-$, $-OC(CH_3)_2CH_2CH_2-$, $-OCH_2C(CH_3)_2CH_2-$, $-OCH_2CH_2C(CH_3)_2-$, $-OCH_2CH=CHCH_2-$, $-OCH_2CH(OH)CH_2CH_2-$, $-OCH_2CH_2CH(OH)CH_2-$, $-OCH_2C(O)CH_2CH_2-$, $-OCH_2CH_2C(O)CH_2-$, or a group of the formula

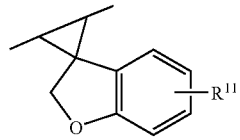

or, where they are attached to adjacent carbon atoms, $R^7$ and $R^8$ may together represent $-OCH_2CH_2-$ or $-OCH_2CH(OH)-$, or $R^7$ and $R^8$ may together form a fused benzene ring;

or, $R^7$ and $R^8$ together form a $C_{1-2}$alkylene bridge across the pyrrolidine, piperidine, morpholine or piperazine ring to which they are attached;

$R^9$ represents hydrogen, benzyl, $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;

$R_{10}$ represents halogen, $C_{1-6}$alkyl, $CH_2OR^c$, oxo, $CO_2R^a$ or $CONR^aR^b$ where $R^a$ and $R^b$ are as previously defined and $R^c$ represents hydrogen, $C_{1-6}$alkyl or phenyl;

$R^{11}$ represents hydrogen, halogen, hydroxy, $C_{1-4}$alkyl, hydroxy$C_{1-4}$alkyl or fluoro$C_{1-4}$alkyl;

n is zero, 1 or 2;

m is 1 or 2; and p is 1, 2 or 3;

and pharmaceutically acceptable salts thereof.

A preferred class of compounds of formula (I) is that wherein $R^1$ is hydrogen, $C_{1-4}$alkyl, $C_{1-4}$alkoxy, halogen or $CF_3$.

Another preferred class of compounds of formula (I) is that wherein $R^2$ is hydrogen, $C_{1-4}$alkyl, $C_{1-4}$alkoxy, halogen or $CF_3$.

Also preferred is the class of compounds of formula (I) wherein $R^3$ is hydrogen, fluorine, chlorine or $CF_3$.

A particularly preferred class of compounds of formula (I) is that wherein $R^1$ is fluorine, chlorine or $CF_3$.

Another particularly preferred class of compounds of formula (I) is that wherein $R^2$ is hydrogen, fluorine, chlorine or $CF_3$.

Also particularly preferred is the class of compounds of formula (I) wherein $R^3$ is hydrogen, fluorine, chlorine or $CF_3$.

Preferably $R^1$ and $R^2$ are in the 3 and 5 positions of the phenyl ring.

More preferably $R^1$ is 3-fluoro or 3-$CF_3$.

More preferably $R^2$ is 5-fluoro or 5-$CF_3$.

More preferably $R^3$ is hydrogen.

Most preferably $R^1$ is 3-F or 3-$CF_3$, $R^2$ is 5-$CF_3$ and $R^3$ is hydrogen.

A further preferred class of compound of formula (I) is that wherein $R^4$ is hydrogen or fluorine.

Another preferred class of compounds of formula (I) is that wherein $R^5$ is hydrogen, fluorine, chlorine or $CF_3$.

Preferably $R^4$ is hydrogen or 3-fluoro and $R^5$ is hydrogen or 4-fluoro.

$R^6$ is preferably $C_{1-4}$alkyl optionally substituted by hydroxy. In particular, $R^6$ is preferably a methyl or hydroxymethyl group. Most especially, $R^6$ is a methyl group.

Another preferred class of compounds of formula (I) is that wherein $R^7$ is hydrogen, hydroxy, $C_{1-2}$alkyl substituted by hydroxy, $C_{1-4}$alkoxy (especially methoxy) or $CO_2R^e$ (where $R^e$ is hydrogen, methyl ethyl or benzyl).

A further preferred class of compounds of formula (I) is that wherein $R^8$ is hydrogen or $C_{1-4}$alkyl (especially methyl).

$R^7$ and $R^8$ are preferably attached to the same carbon atom. In particular, when B represents $CH_2$, both hydrogen atoms in said $CH_2$ moiety are replaced by $R^7$ and $R^8$ forming a moiety of the formula $CR^7R^8$.

Where $R^7$ and $R^8$ are attached to the same carbon atom they may, in particular, together represent —C(O)OCH$_2$CH$_2$—.

In a further preferred class of compounds of formula (I), $R^9$ preferably represents hydrogen, methyl or ethyl. Where A and B both represent $NR^9$, each $R^9$ substituent is independently defined.

Another preferred class of compounds of formula (I) is that wherein $R^{10}$ is methyl.

A further preferred class of compounds of formula (I) is that wherein n is zero.

One favoured group of compounds of the present invention are of the formula (Ia) and pharmaceutically acceptable salts thereof:

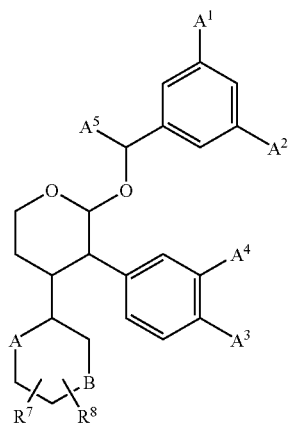

(Ia)

wherein $A^1$ is fluorine or $CF_3$;
$A^2$ is fluorine or $CF_3$;
$A^3$ is fluorine or hydrogen;
$A^4$ is fluorine or hydrogen;
$A^5$ is methyl; and
A, B, $R^7$ and $R^8$ are as defined in relation to formula (I).

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl.

Examples of suitable alkoxy groups include methoxy, ethoxy, n-propoxy, i-propoxy, n-butoxy, s-butoxy and t-butoxy.

As used herein, the terms "fluoroC$_{1-6}$alkyl" and fluoroC$_{1-6}$alkoxy" means a C$_{1-6}$alkyl or C$_{1-6}$alkoxy group in which one or more (in particular, 1 to 3) hydrogen atoms have been replaced by fluorine atoms. Similarly, the term "fluoroC$_{1-4}$alkyl" means a C$_{1-4}$alkyl group in which one or more (in particular 1 to 3) hydrogen atoms have been replaced by fluorine atoms. Particularly preferred are fluoroC$_{1-3}$alkyl and fluoroC$_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

When used herein the term "halogen" means fluorine, chlorine, bromine and iodine. The most apt halogens are fluorine and chlorine of which fluorine is preferred, unless otherwise stated.

Specific compounds within the scope of this invention include:

(2R,3R,4R,8R,10R/S) 2-(1-(1-(3,5-bis(trifluoromethyl)phenyl)ethyl)oxy)-3-(4-fluorophenyl)-4-(N-benzyl-1,2,3,6-tetrahydropyridin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(N-benzylpyrrolidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(pyrrolidin-2-yl)-3,4,5,6-tetrahydropyran;

(2R,3S,4S,8R,10R or 10S) 2-(1-(1-(3,5-bis(trifluoromethyl)phenyl)ethyl)oxy)-3-(4-fluorophenyl)-4-(N-benzylpyrrolidin-2-yl)-3,4,5,6-tetrahydropyran;

(2R,3S,4S,8R,10R or 10S) 2-(1-(1-(3,5-bis(trifluoromethyl)phenyl)ethyl)oxy)-3-(4-fluorophenyl)-4-(pyrrolidin-2-yl)-3,4,5,6-tetrahydropyran;

(2R,3S,4S,8R,10R or S) 2-(1-(1-(3,5-bis(trifluoromethyl)phenyl)ethyl)oxy)-3-(4-fluorophenyl)-4-(piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(N-benzyl-4-hydroxy-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(cis 4-hydroxy-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(trans 4-hydroxy-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(cis 4-hydroxy-N-methyl-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(trans 4-hydroxy-N-methyl-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(cis 4-hydroxy-N-ethyl-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(cis 4-methoxy-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(cis 4-methoxy-N-methyl-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(4-hydroxy-4-methyl-1-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(4-keto-piperidin-2-yl)-3,4,5,6-tetrahydropyran;

(2R,3R,4R,8R,10R)-2-(1-(1-(3,5-bis(trifluoromethyl)phenyl)ethyl)oxy)-3-(4-fluorophenyl)-4-(N-methyl-2-morpholinyl)-3,4,5,6-tetrahydropyran;

(2R,3R,4R,8R,10S)-2-(1-(1-(3,5-bis(trifluoromethyl)phenyl)ethyl)oxy)-3-(4-fluorophenyl)-4-(N-methyl-2-morpholinyl)-3,4,5,6-tetrahydropyran;

(2R,3R,4R,8R,10R and 10S)-2-(1-(1-(3,5-bis(trifluoromethyl)phenyl)ethyl)oxy)-3-(4-fluorophenyl)-4-(N-methyl-3-morpholinyl)-3,4,5,6-tetrahydropyran;

and pharmaceutically acceptable salts thereof

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I) and (Ia) will have the stereochemistry of the 2-, 3-, 4- and 8-positions as shown in formula (Ib) (see, for instance, Examples 11 and 12) and formula (Ic) (see, for instance, Examples 7 and 8)

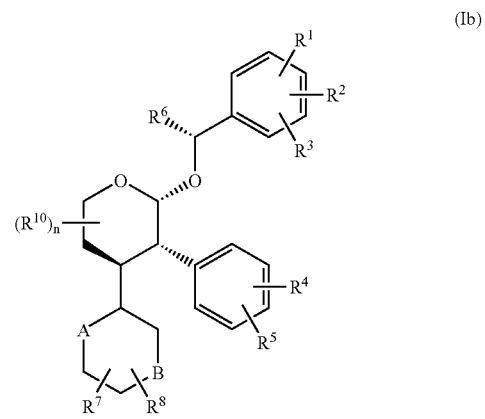
(Ib)

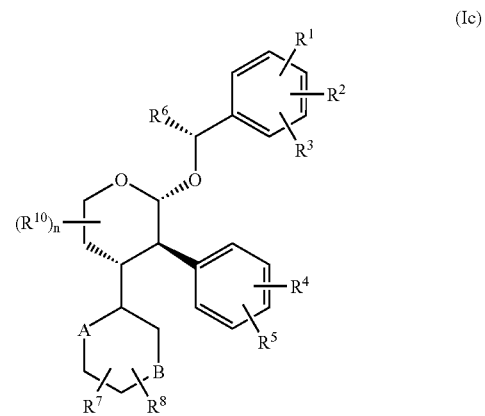
(Ic)

It will be appreciated that the preferred definitions of the various substituents recited herein may be taken alone or in combination and, unless otherwise stated, apply to the generic formula for compounds of the present invention as well as to the preferred classes of compound represented by formula (Ia), formula (Ib) and formula (Ic).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

A more detailed description of pharmaceutical compositions that are suitable for the formulation of compounds of the present invention is disclosed in U.S. Pat. No. 6,071,927, the content of which is incorporated herein by reference (see in particular, column 8, line 50 to column 10, line 4).

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. A comprehensive listing of clinical conditions, uses and methods of treatment for which the compounds of the present invention will be useful is disclosed in U.S. Pat. No. 6,071,927, the content of which is incorporated herein by reference (see, in particular, column 10, line 14 to column 22, line 18).

In particular, the compounds of the present invention are useful in the treatment of a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; and anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

The compounds of the present invention are also particularly useful in the treatment of nociception and pain. Diseases and conditions in which pain predominates, include soft tissue and peripheral damage, such as acute trauma, osteoarthritis, rheumatoid arthritis, musculo-skeletal pain, particularly after trauma, spinal pain, myofascial pain syndromes, headache, migraine, episiotomy pain, and burns.

The compounds of the present invention are also particularly useful in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; in the treatment of inflammatory diseases such as inflammatory bowel disease, psoriasis, fibrositis, osteoarthritis, rheumatoid arthritis, pruritis and sunburn; and in the treatment of allergic disorders such as eczema and rhinitis.

The compounds of the present invention are also particularly useful in the treatment of gastrointestinal (GI) disorders, including inflammatory disorders and diseases of the GI tract such as ulcerative colitis, Crohn's disease and irritable bowel syndrome.

The compounds of the present invention are also particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy; by radiation including radiation therapy such as in the treatment of cancer; and in the treatment of post-operative nausea and vomiting.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), compounds of formula (I) in which A is $NR^9$ and B is $CH_2$ may be prepared by the reaction of a compound of formula (II)

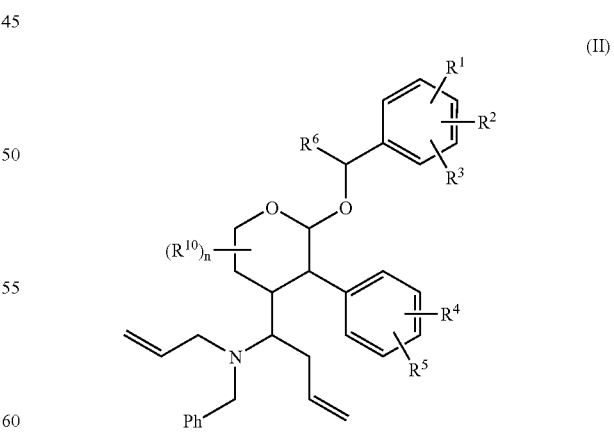

in the presence of a suitable catalyst, and if desired reducing the tetrahydropyridinyl moiety, and also if desired removing or replacing the benzyl moiety.

Suitable catalysts of use in this reaction include any catalyst or multicomponent catalyst system that initiates olefin metathesis. Preferred catalysts are single component metal carbene complexes. Particularly preferred catalysts include:

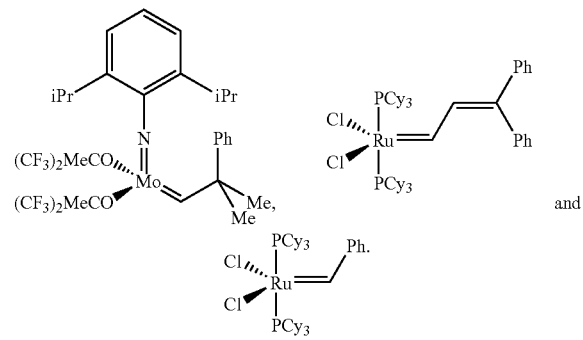

and

An especially preferred catalyst of use in the present invention is $RuCl_2(PCy_3)_2$=CHPh, also referred to as Grubbs' catalyst. These catalysts and their use is described, for instance, in the following literature:

Bazan et al., *J. Am. Chem. Soc.*, 1991, 113, 6899 and references cited therein.
Nguyen et al., *J. Am. Chem. Soc.*, 1992, 114, 3974.
Nguyen and Grubbs, *J. Organomet. Chem.*, 1995, 497, 195
Schwab et al., *Angew. Chem. Int. Ed. Eng.*, 1995, 34, 2039.
Schwab et al., *J. Am. Chem. Soc.*, 1996, 118, 100.
Grubbs and Chang, *Tetrahedron*, 1998, 54, 4413.

Suitable organic solvents of use in the reaction include halogenated hydrocarbons, such as dichloromethane or chloroform.

The reaction is conveniently effected at room temperature and pressure, for example at about 20° C.

Reduction of the tetrahydropyridinyl moiety may be effected by conventional methodology, for example, by catalytic hydrogenation in the presence of a suitable catalyst such as palladium on carbon, in a suitable solvent such as an alcohol, for example, methanol. These conditions will also conveniently remove the benzyl moiety ($R^9$) which may be replaced using conventional methodology.

According to another general process (B), compounds of formula (I) in which A is $NR^9$ and B is a bond may be prepared by the reaction of a compound of formula (III)

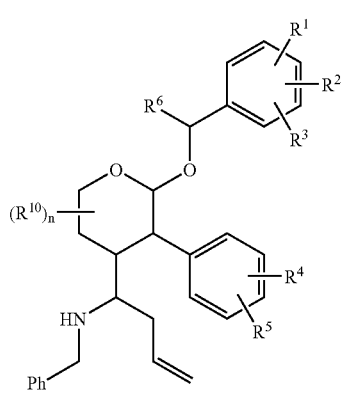

(III)

under reducing conditions, for instance, in the presence of borane or borane.tetrahydrofuran complex, followed by treatment with hydrogen peroxide and a base such as sodium hydroxide. The reaction is conveniently effected in a solvent such as an ether, for example, tetrahydrofuran.

If desired, the benzyl moiety ($R^9$) may be removed as described above.

According to another general process (C), compounds of formula (I) in which A is $NR^9$ and B is O may be prepared by the reaction of a compound of formula (IV)

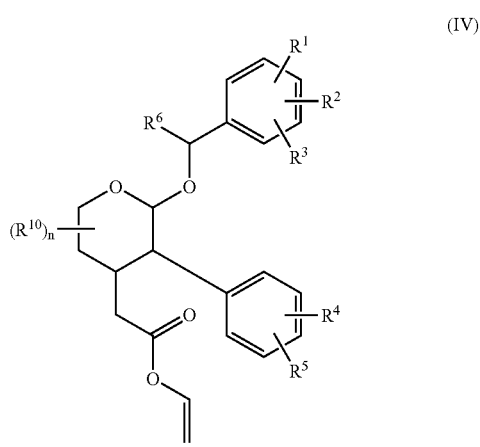

(IV)

with an amine of the formula $R^9NH_2$, followed by reduction of the keto function using a suitable reducing agent such as a borohydride, for example sodium cyanoborohydride. The reduction is conveniently effected in a solvent such as an ether, for example, tetrahydrofuran.

According to another general process (D), compounds of formula (I) in which A is O and B is $NR^9$ may be prepared by the reaction of a compound of formula (V)

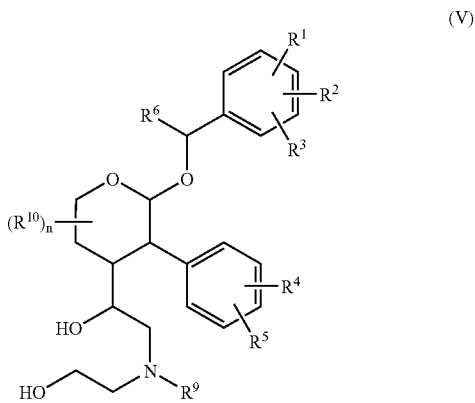

(V)

under suitable dehydrating conditions, for example, using triphenylphosphine and diethylazodicarboxylate in a suitable solvent such as tetrahydrofuran, at an elevated temperature such as at reflux, or alternatively using methanesulfonyl chloride or benzenesulfonyl chloride in pyridine or triethylamine, in a suitable organic solvent such as dichloromethane, conveniently at a temperature between room temperature and 80° C.

According to another general process (E), compounds of formula (I) may be prepared by the reaction of a compound of formula (VI) with a compound of formula (VII)

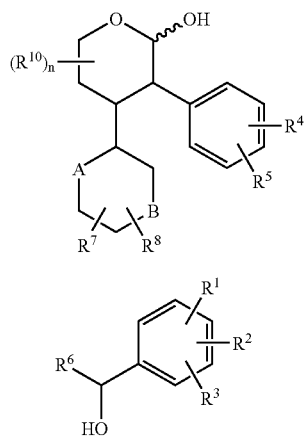

(VI)

(VII)

preferably in the presence of a resin catalyst such as Amberlyst™ 15, and 3 Angstrom molecular sieves.

The reaction is conveniently effected in a suitable solvent such as a halogenated hydrocarbon, for example, dichloromethane, conveniently at room temperature.

According to another general process (F), compounds of formula (I), in which $R^6$ is either methyl or hydroxymethyl, may be prepared by the reaction of a compound of formula (VIII)

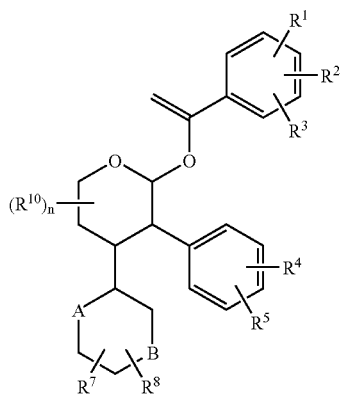

(VIII)

under either:

(a) (where $R^6$ is methyl) catalytic hydrogenation conditions (e.g. $H_2$, $Pd(OH)_2$ on carbon) in a suitable solvent such as an ester, for example, ethyl acetate; or (b) (where $R^6$ is hydroxymethyl) reducing conditions (e.g. borane or $BH_3$.THF) followed by treatment with hydrogen peroxide and a base such as sodium hydroxide, conveniently in a solvent such as an ether, for example, tetrahydrofuran.

Further details of suitable procedures will be found in the accompanying Examples.

Compounds of formula (II) may be prepared from a compound of formula (III) above, by N-alkylation with an allyl halide, for example, allyl bromide. The reaction is preferably effected in the presence of an inorganic base such as potassium carbonate and a suitable solvent such a dimethylformamide. The reaction is conveniently effected at a temperature between room temperature and 100° C.

Compounds of formula (III) may be prepared from a compound of formula (IX)

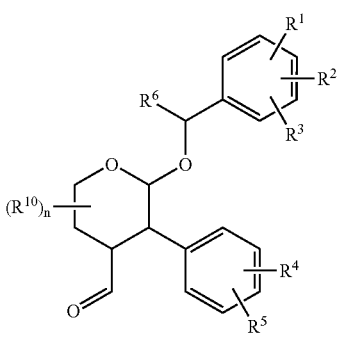

(IX)

by reaction with benzylamine in a suitable solvent such as a halogenated hydrocarbon, for example, dichloromethane. Following basification, using for example basic alumina, the reaction mixture is filtered, evaporated and the residue dissolved in a suitable solvent such as an ether, for example, tetrahydrofuran. Reaction with a suitable alkylating reagent such as a Grignard reagent, for example, allyl magnesium bromide, in the presence of a suitable solvent such as an ether, for example, diethyl ether, affords the compound of formula (III).

Compounds of formula (IX) may be prepared from a compound of formula (X)

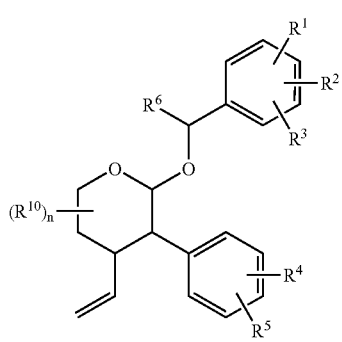

(X)

by an ozonolysis reaction, using ozone at a low temperature, for example, between −60° C. and −100° C., in a suitable solvent such as a halogenated hydrocarbon, for example, dichloromethane, or an alcohol, for example, methanol, or a mixture thereof The intermediate ozonide thus formed need not be isolated but instead is decomposed using a suitable reducing agent, for example, dimethyl sulfide, trimethyl phosphite or thiourea.

Compounds of formula (X) may be prepared from known starting materials, for example as described in International (PCT) patent publication No. WO 00/56727, using conventional methodology, such as the method of general process (E) above.

Compounds of formula (IV) may be prepared from a compound of formula (XI)

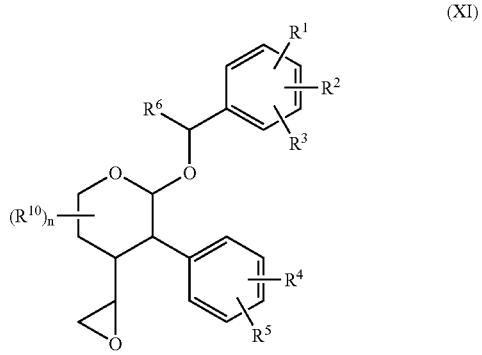

(XI)

by reaction with allyl alcohol in the presence of a suitable reducing reagent, such as a hydride, for example sodium hydride, in a suitable solvent such as an ether, for example tetrahydrofuran, at an elevated temperature, for example, between 60° C. and 100° C., followed in a second step by an oxidation reaction, for example using a mild oxidizing reagent such as Dess-Martin periodinane, in a suitable solvent such as a halogenated hydrocarbon, for example dichloromethane, conveniently at room temperature.

Compounds of formula (XI) may be prepared from a compound of formula (X) by an epoxidization reaction using a peracid, for example, m-chloroperbenzoic acid. The reaction is effected in a solvent such as a halogenated hydrocarbon, for example, dichloromethane, conveniently at room temperature.

Compounds of formula (V) may be prepared from a compound of formula (XI) by reaction with a suitable amine of the formula $R^9NHCH_2CH_2OH$. The reaction is conveniently effected in a solvent such as an alcohol, for example methanol, at an elevated temperature, for example at the reflux temperature of the solvent.

Compounds of formula (VI) may be prepared by the reduction of a compound of formula (XII)

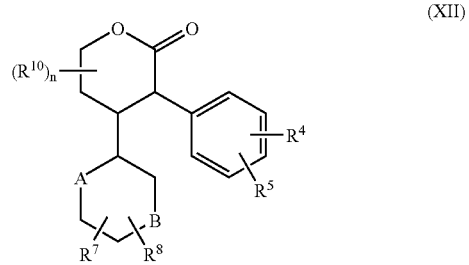

(XII)

using conventional conditions such as sodium borohydride in the presence of a transition metal catalyst such as cerium chloride hexahydrate, in a solvent such as alcohol, for example, ethanol; or using DiBAL in a solvent such as a halogenated hydrocarbon, for example, dichloromethane.

Compounds of formula (XII) may be prepared from a compound of formula (XIII)

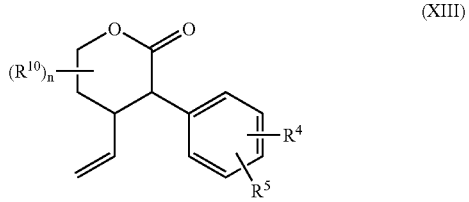

(XIII)

by a variety of methods such as those described herein.

Compounds of formula (VIII) may be prepared by the reaction of a compound of formula (XIV)

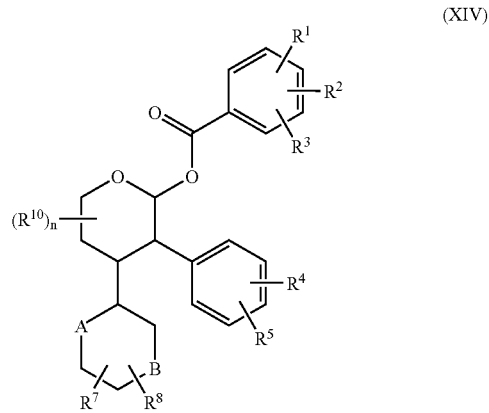

(XIV)

with dimethyltitanocene in a solvent such as toluene, pyridine or tetrahydrofuran, or a mixture thereof.

Compounds of formula (XIV) may be prepared by the reaction of a compound of formula (XII) with L-Selectride™ (lithium tri-sec-butylborohydride) followed by treatment with a compound of formula (XV)

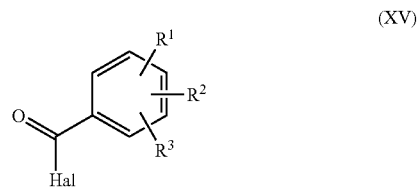

(XV)

wherein Hal is a halogen atom, preferably chlorine.

Compounds of formula (VII) and (XV) are either known compounds or may be prepared by methods readily available to a person of ordinary skill in the art.

It will be appreciated that the general methodology described above may be adapted, using methods that are readily apparent to one of ordinary skill in the art, in order to prepare further compounds of the present invention. In particular, compounds of formula (I) may be interconverted into further compounds of formula (I) using conventional synthetic techniques such as N-alkylation or O-alkylation, oxidation or reduction. Such reactions are illustrated in the examples hereinafter.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 100 nM on said test method.

The following non-limiting Examples serve to illustrate the preparation of compounds of the present invention:

DESCRIPTION 1

(2R,3S,4R,8R)-2-(1-(1-(3,5-Bis(trifluoromethyl)phenyl)ethyl)oxy)-3-(4-fluorophenyl)-4-vinyl-3,4,5,6-tetrahydropyran; and (2R,3R,4S,8R)-2-(1-(1-(3,5-Bis(trifluoromethyl)phenyl)oxy)-3-(4-fluorophenyl)-4-vinyl-3,4,5,6-tetrahydropyran A solution of a mixture of lactol isomers of (±) 3,4-trans-3-(4-fluorophenyl)-4-vinyl-3,4,5,6-tetrahydropyran-2-ol (see PCT Publication No. WO 00/5672 at page 45; 48.8 g, 0.219 mol) and (R)-1-(3,5-bis(trifluoromethyl)phenyl)ethanol (50 g, 0.203 mol) in dichloromethane (10 ml) was stirred with Amberlyst™ 15 resin (10 g) and 3 Å molecular sieves (15 g) at 0° C. for 72 hours. The solution was filtered, evaporated to dryness and the residue purified by column chromatography on silica gel (eluting with increasing amounts of dichloromethane in isohexane, 0–20%) to afford the title compounds.

Isomer 1 (12.8 g)—(2R,3S,4R,8R) 3,4-trans-2,3-cis (earliest eluting isomer): $^1$H NMR (400 MHz, CDCl$_3$) δ 1.46 (3H, d J 6.6 Hz), 1.67–1.78(1H, m), 1.82(1H, d J 13.3 Hz), 2.70(1H, dd J 12.0 Hz and 3.2 Hz), 3.05–3.14(1H, m), 3.76(1H, dm J 11.2 Hz), 4.05(1H, td J 10.9 Hz and 2.8 Hz), 4.44(1H. d J 3.2 Hz), 4.86–4.91(2H, m), 4.96(1H, d J 16.2 Hz), 5.48(1H, m), 6.97(2H, apparent t J 8.7 Hz), 7.15(2H, m), 7.20(2H, s), 7.62(1H, s).

Isomer 2 and 3 (16 g) and

Isomer 4 (12.4 g)—(2R,3R,4S,8R) 3,4-trans-2,3-trans (latest eluting isomer): $^1$H NMR (360 MHz, CDCl$_3$) δ 1.38(3H, d J 6.6 Hz), 1.69(2H, m), 2.41(1H, m), 2.51(1H, dd J 11.6 Hz and 8.3 Hz), 3.57(1H, m), 4.13(1H, dt J 11.8 Hz and 3.0 Hz), 4.16(1H, d J 8.2 Hz), 4.79(2H, m), 4.96(1H, q J 6.6 Hz), 5.45(1H, m), 6.90–7.00(4H, m), 7.19(2H, s), 7.68(1H, s).

DESCRIPTION 2

(2R,3R,4R,8R) 2-(1-(1-(3,5-Bis(trifluoromethyl)phenyl)ethyl)oxy)-3-(4-fluorophenyl)-4-formyl-3,4,5,6-tetrahydropyran Through a cooled solution (−80° C.) of (2R,3R,4S,8R) 2-(1-(1-(3,5-bis(trifluoromethyl)phenyl)ethyl)oxy)-3-(4-fluorophenyl)-4-vinyl-3,4,5,6-tetrahydropyran (isomer 4, Description 1; 2 g) dissolved in methanol (15 ml) and dichloromethane (15 ml) was bubbled ozone until the solution turned blue. After purging the solution with oxygen followed by nitrogen, dimethyl sulphide (3 ml) was added and the solution stirred at room temperature overnight. The solution was evaporated and the residue was purified on silica gel (eluting with 10% and 20% ethyl acetate in isohexane) to give the title compound as an oil which crystallized on standing.

DESCRIPTION 3

(2R,3R,4R,8R,10R and 10S) 2-(1-(1-(3,5-Bis(trifluoromethyl)phenyl)-ethyl)oxy)-3-(4-fluorophenyl)-4-((1-benzylamino)but-3-enyl)-3,4,5,6-tetrahydropyran To a mixture of (2R,3R,4R,8R) 2-(1-(1-(3,5-bis(trifluoromethyl)phenyl)ethyl)oxy)-3-(4-fluorophenyl)-4-formyl-3,4,5,6-tetrahydropyran (Description 2; 0.44 g) and benzylamine (102 mg) in dichloromethane (5 ml) was added basic alumina (0.3 g).

After 30 minutes the solution was filtered and the filtrate evaporated. The residue from evaporation was dissolved in tetrahydrofuran (5 ml) and this solution was added to a cooled (−20° C.) solution of allyl magnesium bromide in diethyl ether (1M, 5 ml) and tetrahydrofuran (5 ml). After 30 minutes at −20° C. the solution was quenched by addition of saturated ammonium chloride and the product extracted with ethyl acetate. After drying (MgSO$_4$) and evaporating to dryness the residue was purified by chromatography on silica gel (eluting with increasing concentrations of ethyl acetate in isohexane (10%, 20%, 30%)) to give the title compound as a (3:2) mixture of C-10 epimers by $^1$H NMR. MS m/z 596(M+H).

DESCRIPTION 4

(2R,3S,4S,8R,10R and 10S) 2-(1-(1-(3,5-Bis(trifluoromethyl)phenyl)-ethyl)oxy)-3-(4-fluorophenyl)-4-((1-benzylamino)but-3-enyl)-3,4,5,6-tetrahydropyran The title compound was prepared from isomer 1 of Description 1 (3,4-trans,2,3-cis isomer) using procedures analogous to those described in Description 2 and Description 3 as a mixture of C-10 epimers (approximately 1:1) by $^1$H NMR. MS m/z 596(M+H).

DESCRIPTION 5

(2R,3R,4R,8R,10R and 10S) 2-(1-(1-(3,5-Bis(trifluoromethyl)phenyl)-ethyl)oxy)-3-(4-fluorophenyl)-4-((1-(N-benzyl-N-allyl)amino)but-3-enyl)-3,4,5,6-tetrahydropyran The compound prepared in Description 3 (0.345 g) was treated with allyl bromide (0.332 ml) and potassium carbonate (0.9 g) in dimethylformamide (3 ml) for 72 hours at room temperature, at 60° C. for 5 hours and at 100° C. for 12 hours. Ethyl acetate was added and the organic solution was washed with water (5 times), then with saturate brine and dried (MgSO$_4$). After removal of the solvent in vacuo the residue was chromatographed on silica gel eluting with 10% ethyl acetate in isohexane to give the title compound as a mixture of epimers (approx 1:1 by $^1$H NMR) MS m/z 636(M+H).

DESCRIPTION 6

(2R,3R,4R,8R,10R and 10S) 2-(1-(1-(3,5-Bis(trifluoromethyl)phenyl)-ethyl)oxy)-3-(4-fluorophenyl)-4-(N-benzyl-4-oxo-1,2,3,4-tetrahydropyridin-2-yl)-3,4,5,6-tetrahydropyran A solution of (2R,3R,4R,8R) 2-(1-(1-(3,5-bis(Trifluoromethyl)phenyl)ethyl)oxy)-3-(4-fluorophenyl)-4-formyl-3,4,5,6-tetrahydropyran (Description 2; 400 mg, 0.862 mmol) in acetonitrile (2.5 ml) was treated with alumina (1.20 g) and then benzylamine (98.6 µl, 0.905 mmol). The mixture was stirred at room temperature for 1 hour, then the alumina removed by filtration. Indium(III) trifluoromethanesulphonate (3 mol %, 14.5 mg, 25.9 nmol) was added followed by 1-methoxy-3-trimethylsilyloxy-1,3-butadiene (250 µl, 1.29 mmol) and the mixture was stirred at room temperature.

After 2 hours the mixture was diluted with saturated aqueous sodium hydrogen carbonate (40 ml) and was extracted with ethyl acetate (2×40 ml). The combined organic phases were dried (MgSO$_4$) and evaporated in vacuo to give a crude oil (433 mg). This material was chromatographed on silica, eluting with 40–100% ethyl acetate in hexanes to give the title compound as a single isomer (307 mg, 57%). $^1$H NMR (360 MHz, CDCl$_3$) δ 1.38 (3H, d, J 6.6 Hz), 1.79–1.88 (2H, m), 1.91–1.97 (1H, m), 2.03–2.09 (1H, m), 2.55–2.62 (1H, m), 2.83 (1H, dd, J 11.7 Hz and 7.9 Hz), 3.33 (1H, d, J 8.7 Hz), 3.44 (1H, dt, J 11.6 Hz and J 3.5 Hz), 3.99 (1H, d, J 7.9 Hz), 4.11–4.14 (1H, m), 4.20 (1H, d, J 14.9 Hz), 4.38 (1H, d, J 14.9 Hz), 4.89–4.97 (2H, m), 6.91–6.93 (2H, m), 7.00–7.07 (3H, m), 7.11–7.14 (4H, m), 7.26–7.28 (3H, m), 7.67 (1H, s); m.s. (ES$^+$), 622 (M$^+$+H), 364 (M$^+$−257).

EXAMPLE 1

(2R,3R,4R,8R,10R/S) 2-(1-(1-(3,5-Bis(trifluoromethyl)phenyl)ethyl)oxy)-3-(4-fluorophenyl)-4-(N-benzyl-1,2,3,6-tetrahydropyridin-2-yl)-3,4,5,6-tetrahydropyran (isomer 1); and

EXAMPLE 2

(2R,3R,4R,8R,10S/R) 2-(1-(1-(3,5-Bis(trifluoromethyl)phenyl)ethyl)oxy)-3-(4-fluorophenyl)-4-(N-benzyl-1,2,3,6-tetrahydropyridin-2-yl)-3,4,5,6-tetrahydropyran (isomer 2)

To a solution of the mixture of epimeric (2R,3R,4R,8R, 10R and 10S) 2-(1-(1-(3,5-bis(trifluoromethyl)phenyl)ethyl)oxy)-3-(4-fluorophenyl)-4-((1-(N-benzyl-N-allyl)amino)but-3-enyl)-3,4,5,6-tetrahydropyran (Description 5; 0.247 g) in dichloromethane (50 ml) was added bis(tricyclohexylphosphine)benzylidine ruthenium (IV) dichloride (Grubbs' catalyst, 0.016 g). After 15 minutes the solution was evaporated to dryness and the residue was chromatographed on silica gel (eluting with dichloromethane followed by 10% ethyl acetate in dichloromethane to give the two separate isomers of 2-(1-(1-(3,5-bis(trifluoromethyl)phenyl)ethyl)oxy)-3-(4-fluorophenyl)-4-(N-benzyl-1,2,3,6-tetrahydropyridin-2-yl)-3,4,5,6-tetrahydropyran.

EXAMPLE 1 (isomer 1) free base—$^1$H NMR (400 MHz, CDCl$_3$) δ 1.35(3H, d J 6.6 Hz), 1.5 (1H, m), 1.77(2H, m), 1.95(1H, m), 2.05(1H, m), 2.71(1H, dd J 9.8 Hz and 7.4 Hz), 2.80(1H,m), 2.93(1H, d 18.4 Hz), 3.07(1H, d 18.4 Hz), 3.49(1H, td J 11.4 Hz and 2.32 Hz), 3.52(1H, d J 13.6 Hz), 3.60(1H, d J 13.7 Hz), 4.11(1H, m), 4.17(1H, d J 7.04 Hz), 4.90(1H q J 6.7 Hz), 5.45(1H, dm J 10.1 Hz), 5.55(1H, dm J 10.2 Hz), 6.91(2H, apparent t J 8.6 Hz), 7.08(2H, dd J 8.6 and 5.5 Hz), 7.22(2H,s), 7.23–7.31(5H, m), 7,67(1H, s). MS m/z 608 (M+H).

The hydrochloride salt was formed by addition of 1M HCl in diethyl ether and evaporation to a solid.

EXAMPLE 2 (isomer 2) free base—$^1$H NMR (400 MHz, CDCl$_3$) δ 1.36(3H, d J 6.7 Hz), 1.6(1H, m), 1.79(2H, m), 2.01(1H, m), 2.25(2H, m), 2.46(1H, m), 2.49(1H, d J 16.8 Hz), 2.66(1H, dd J 11.3 Hz and 8.2 Hz), 2.93(1H, d J 12.9 Hz), 2.97(1H, m), 3.50(1H, td J 11.3 Hz and 3.1 Hz), 4.02(1H, d J 12.9 Hz), 4.15(1H, d J 7.8 Hz), 4.95(1H apparent q J 6.3 Hz), 5.48(1H, dm J 10.1 Hz), 5.65(1H, dm J 9.4 Hz), 6.94(2H, apparent t J 8.6 Hz), 7.03(2H, dd J 8.6 Hz and 5.5 Hz), 7.16(2H, s), 7.21–7.28(5H, m), 7.68(1H, s). MS m/z 608 (M+H)

The hydrochloride salt was formed by addition of 1M HCl in diethyl ether and evaporation to a solid.

EXAMPLE 3

(2R,3R,4R,8R,10R or 10S) 2-(1-(1-(3,5-Bis(trifluoromethyl)phenyl)-ethyl)oxy)-3-(4-fluorophenyl)-4-(piperidin-2-yl)-3,4,5,6-tetrahydropyran (isomer 1)

A solution of the hydrochloride salt of isomer 1 (Example 1; 134 mg) dissolved in methanol was hydrogenated in the presence of 10% palladium on carbon (40 mg) for 72 hours at 40 psi. The solution was filtered and the solvent was removed. A solution of the residue in ethyl acetate was washed with 10% potassium carbonate, dried (MgSO$_4$) and the solvent removed by evaporation. The product was purified by chromatography on silica gel eluting with mixtures of dichloromethane containing 1%, 2% and 4% of a solution of methanol/aqueous ammonia/dichloromethane (10:0.4:90).

The product was crystallized as the HCl salt from isohexane to give the title compound. $^1$H NMR (360 MHz, CD$_3$OD d$_4$) δ 1.35(4H, d J 6.6 Hz), 1.48–1.68(4H, m), 1.78(3H, m), 2.22(1H, tm J 12.2 Hz), 2.64(1H, d J 10.4 Hz), 2.75(2H, dd J 12.2 Hz and 8.5 Hz), 3.35(1H, d J 12.4 Hz), 3.66(1H, td J 11.8 Hz and 1.6 Hz), 4.18(1H, dd J 11.8 Hz and 3.1 Hz), 4.33(1H, d J 8.0 Hz), 5.02(1H, apparent q J 6.5 Hz), 7.01(2H, apparent t J 8.7 Hz), 7.22(2H, dd J 8.7 and 5.5 Hz), 7.32(2H,s), 7.74(1H, s). MS m/z 520 (M+H).

EXAMPLE 4

(2R,3R,4R,8R,10S or 10R) 2-(1-(1-(3,5-Bis(trifluoromethyl)phenyl)ethyl)-oxy)-3-(4-fluorophenyl)-4-(piperidin-2-yl)-3,4,5,6-tetrahydropyran (isomer 2)

Prepared according to the method of Example 3, above, except using isomer 2 from Example 2 as starting material. $^1$H NMR (360 MHz, MeOD d$_4$) δ 1.21(1H,m), 1.33(3H, d J 6.6 Hz), 1.48(1H, qd J 12.3 Hz and 2.1 Hz), 1.56–1.70 (3H, m), 1.77(1H, broad d J 14.7 Hz), 1.91(2H, broad apparent t J 15.2 Hz), 2.21–2.29(1H, m), 2.55(1H, dt J 12.3 Hz and 2.4 Hz), 2.63(1H, dd J 11.8 Hz and 8.1 Hz), 2.80(1H, td J 12.8 Hz and 3.2 Hz), 3.28(1H, broad d), 3.61–3.68(1H, m), 4.17(1H dt J 11.3 Hz and 2.6 Hz), 4.36(1H, d J 8.1 Hz), 5.02(1H, q J 6.6 Hz), 7.01(2H,apparent t J 8.7 Hz), 7.17(2H, dd J 8.4 Hz and 5.3 Hz), 7.32(2H, s), 7.75(1H, s).

EXAMPLE 5

(2R,3R,4R,8R,10R or 10S) 2-(1-(1-(3,5-Bis(trifluoromethyl)phenyl)-ethyl)oxy)-3-(4-fluorophenyl)-4-(N-benzylpyrrolidin-2-yl)-3,4,5,6-tetrahydropyran (isomer 1); and

EXAMPLE 6

(2R,3R,4R,8R,10S or 10R) 2-(1-(1-(3,5-Bis(trifluoromethyl)phenyl)-ethyl)oxy)-3-(4-fluorophenyl)-4-(N-benzylpyrrolidin-2-yl)-3,4,5,6-tetrahydropyran (isomer 2)

a) To a cooled (−20° C.) solution of the mixture of epimeric 2-(1-(1-(3,5-bis(trifluoromethyl)phenyl)ethyl)

oxy)-3-(4-fluorophenyl)-4-((1-benzylamino)but-3-enyl)-3, 4,5,6-tetrahydropyran (Description 3;, 0.39 g ) in tetrahydrofuran (10 ml) was added 1M borane tetrahydrofuran complex (2 ml, 2 mmol). The solution was stirred at room temperature for 1.5 hours then 1M NaOH (20 ml) containing 27% hydrogen peroxide (0.1 ml) was slowly added. After 20 minutes, water (20 ml) was added and the solution was extracted with ethyl acetate. The organic phase was washed with aqueous sodium bisulphite and was dried (MgSO$_4$). After evaporation a solution of the residue in methanol was stirred with potassium carbonate (0.3 g) for 72 hours. After evaporation water and ethyl acetate were added and the organic phase was dried (MgSO$_4$). The solvent was removed by evaporation and the residue was purified by chromatography on silica gel (eluting with ethyl acetate followed by 10% methanol in ethyl acetate) to give (2R,3R,4R,8R,10R and 10S) 2-(1-(1-(3,5-bis(trifluoromethyl)phenyl)ethyl)oxy)-3-(4-fluorophenyl)-4-((1-benzylamino)-4-hydroxybutyl)-3,4,5,6-tetrahydropyran as a mixture of epimers (2:1).

b) A solution of the mixture of epimers from step (a) (249 mg) in dichloromethane (20 ml), triphenylphosphine (159 mg) and carbon tetrabromide (202 mg) was heated under reflux for 30 minutes. The cooled solution was evaporated and ethyl acetate and aqueous potassium carbonate added. The organic phase was dried (MgSO$_4$), evaporated and purified by chromatography on silica gel (eluting with hexane followed by 5% ethyl acetate in isohexane to give isomer 1 (Example 5) followed by 10% and 20% ethyl acetate in isohexane to give isomer 2 (Example 6).

EXAMPLE 5 (isomer 1) free base—MS m/z 596 (M+H).

EXAMPLE 6 (isomer 2) hydrochloride salt from diethyl ether—MS m/z 596 (M+H).

EXAMPLE 7

(2R,3R,4R,8R,10R or 10S) 2-(1-(1-(3,5-Bis(trifluoromethyl)phenyl)ethyl)-oxy)-3-(4-fluorophenyl)-4-(pyrrolidin-2-yl)-3,4,5,6-tetrahydropyran (isomer 1)

(2R,3R,4R,8R,10R or 10S) 2-(1-(1-(3,5-Bis(trifluoromethyl)phenyl)ethyl)oxy)-3-(4-fluorophenyl)-4-(N-benzylpiperidin-2-yl)-3,4,5,6-tetrahydropyran isomer 1 (Example 5; 130 mg) was converted to its hydrochloride salt by dissolving in dichloromethane (5 ml) addition of 1M HCl in diethyl ether followed by evaporation. A solution of the residue dissolved in methanol (20 ml) was hydrogenated in the presence of 10% palladium on carbon (30 mg) at 40 psi for 16 hours. The solution was filtered, evaporated and the residue was partitioned between ethyl acetate and aqueous potassium carbonate. The organic phase was dried (MgSO$_4$), evaporated and the residue purified by chromatography on silica gel eluting with mixtures of dichloromethane and 0%, 10%, 20%, 40% and 100% solution of dichloromethane:methanol:aqueous ammnonia (90:10:0.4) to give the title compound as an oil.

$^1$H NMR (360 MHz, CDCl$_3$) δ 1.09–1.20(1H,m), 1.35 (3H, d J 6.7 Hz), 1.45–1.63(2H, m), 1.69(1H, m), 1.74–1.86 (1H, m), 1.92(1H, v broad s),2.66(1H, dd J 11.2 Hz and 8.4 Hz), 2.72(2H, m), 2.84(1H, m), 3.52(1H, m), 4.15(2H, m&d J 8.4 Hz), 4.93(1H, q J 6.3 Hz), 6.93(2H, apparent t J 8.4 Hz),7.01(2H, dd J 8.4 Hz and 5.3 Hz), 7.18(2H, s), 7.67(1H, s). MS m/z 506 (M+H).

The hydrochloride salt was crystallized from diethyl ether.

EXAMPLE 8

(2R,3R,4R,8R,10S or 10R) 2-(1-(1-(3,5-Bis(trifluoromaethyl)phenyl)ethyl)-oxy)-3-(4-fluorophenyl)-4-(pyrrolidin-2-yl)-3,4,5,6-tetrahydropyran (isomer 2)

The title compound was prepared using a method analogous to that described in Example 7 using as starting material (2R,3R,4R,8R,10S or 10R) 2-(1-(1-(3,5-bis(trifluoromethyl)phenyl)ethyl)oxy)-3-(4-fluorophenyl)-4-(N-benzylpiperidin-2-yl)-3,4,5,6-tetrahydropyran isomer 2 (Example 6).

$^1$H NMR (360 MHz, CDCl$_3$) δ 1.36(3H, d J 6.3 Hz), 1.40–1.50(1H, m), 1.52–1.60(3H, m), 1.70(1H, m), 1.87(1H, v broad s), 2.08(1H, m), 2.48(1H dd J 11.9 Hz and 8.4 Hz), 2.64–2.74(2H, m), 2.83(1H, m), 3.53(1H, td J 11.9 Hz and 2.1 Hz), 4.16(2H, m&d J 8.4 Hz), 4.93(1H, q J 6.7 Hz), 6.94(2H, apparent t J 8.8 Hz), 7.03(2H, dd J 8.4 Hz and 5.3 Hz), 7.16(2H, s), 7.67(1H, s). MS m/z 506(M+H).

EXAMPLE 9

(2R,3S,4S,8R,10R or 10S) 2-(1-(1-(3,5-Bis(trifluoromethyl)phenyl)-ethyl)oxy)-3-(4-fluorophenyl)-4-(N-benzylpyrrolidin-2-yl)-3,4,5,6-tetrahydropyran (isomer 1); and

EXAMPLE 10

(2R,3S,4S,8R,10S or 10R) 2-(1-(1-(3,5-Bis(trifluoromethyl)phenyl)-ethyl)oxy)-3-(4-fluorophenyl)-4-(N-benzylpyrrolidin-2-yl)-3,4,5,6-tetrahydropyran (isomer 2)

a) To a cooled (−20° C.) solution of the mixture of epimeric (2R,3S,4S,8R,10R and 10S) 2-(1-(1-(3,5-bis(trifluoromethyl)phenyl)ethyl)oxy)-3-(4-fluorophenyl)-4-((1-benzylamino)but-3-enyl)-3,4,5,6-tetrahydropyran (Description 4; 0.39 g) in tetrahydrofuran (10 ml) was added 1M borane. Tetrahydrofuran complex (2 ml, 2 mmol). The solution was stirred at room temperature for 1.5 hours then 1M-NaOH (20 ml) containing 27% hydrogen peroxide (0.1 ml) was slowly added. After 20 minutes, water (20 ml) was added and the solution was extracted with ethyl acetate. The organic phase was washed with aqueous sodium bisulphite and was dried (MgSO$_4$). After evaporation a solution of the residue in methanol was stirred with potassium carbonate (0.3 g) for 72 hours. After evaporation water and ethyl acetate were added and the organic phase was dried (MgSO$_4$). The solvent was removed by evaporation and the residue was purified by chromatography on silica gel (eluting with ethyl acetate followed by 10% methanol in ethyl acetate) to give (2R,3S,4S,8R,10R and 10S) 2-(1-(1-(3,5-bis(trifluoromethyl)phenyl)ethyl)oxy)-3-(4-fluorophenyl)-4-((1-benzylamino)-4-hydroxybutyl)-3,4,5,6-tetrahydropyran as a mixture of C-10 epimers (2:1).

b) A solution of the mixture of epimers from step (a) (249 mg) in dichloromethane (20 ml), triphenylphosphine (159 mg) and carbon tetrabromide (202 mg) was heated under reflux for 30 minutes. The cooled solution was evaporated and ethyl acetate and aqueous potassium carbonate added. The organic phase was dried (MgSO$_4$), evaporated and purified by chromatography on silica gel (eluting with hexane followed by 5% ethyl acetate in isohexane to give isomer 1 (Example 9) followed by elution with 10% and 20% ethyl acetate in isohexane to give isomer 2 (Example 10).

EXAMPLE 9 (isomer 1): ¹H NMR (360 MHz, CDCl₃) δ 1 43(3H, d J 6.7 Hz), 1.60(3H, m), 1.72(1H, broad d J 13.3 Hz), 1.96(1H, m), 2.11(2H, m), 2.49(1H broad t J 11.9 Hz), 2.77(2H, m), 3.05(2H, m+d J 14 Hz), 3.68(1H, d J 13.6 Hz), 3.83(1H, dd J 11.2 Hz and 4.2 Hz), 4.03 (1H, td J 10.9 Hz and 2.4 Hz), 4.39(1H, d J 3.2 Hz), 4.86(1H, q J 6.3 Hz),6.97(2H, apparent t J 8.4 Hz), 7.1–7.33(9H, m), 7.60 (1H, s).

MS m/z 596 (M+H).

EXAMPLE 10 (isomer 2): MS m/z 596 (M+H).

EXAMPLE 11

(2R,3S,4S,8R,10R or 10S) 2-(1-(1-(3,5-Bis(trifluoromethyl)phenyl)-ethyl)oxy)-3-(4-fuorophenyl)-4-(pyrrolidin-2-yl)-3,4,5,6-tetrahydropyran (isomer 1)

The product of Example 9 was hydrogenated by a procedure analogous to that described in Example 3 to give the title compound.

¹H NMR (360 MHz, CDCH) δ 1.37(1H, m), 1.46(3H, d J 6.7 Hz), 1.49–1.57(1H,m), 1.52–1.79(4H, m), 2.44(1H, m), 2.71–2.80(2H, m), 2.85–2.92(2H, m), 2.80(1H,m), 10.8 Hz), 4.02(1H, td J 10.9 Hz and 4.5 Hz), 4.39(1H, d J 3.1 Hz), 4.89(1H, q J 6.7 Hz), 6.99(2H, apparent t J 8.8 Hz), 7.22–7.26(4H, m), 7.61(1H, s).

EXAMPLE 12

(2R,3S,4S,8R,10S or 10R) 2-(1-(1-(3,5-Bis(trifluoromethyl)phenyl)ethyl)-oxy)-3-(4-fluorophenyl)4-(pyrrolidin-2-yl)-3,4,5,6-tetrahydropyran (isomer 2)

The product of Example 10 was hydrogenated by a procedure analogous to that described in Example 3 to give the title compound.

¹H NMR (360 MHz, CDCl₃) δ 1.42(1H, m), 1.46(3H, d J 6.3 Hz), 1.49–1.69(2H, m), 1.85(1H broad d J 12.9 Hz), 2.04(2H, vbroad s), 2.64(1H, dd J 11.9 Hz and 2.8 Hz), 2.73(2H, m), 2.90(2H, m), 3.79(1H, dd J 11.2 Hz and 3.9 Hz), 4.04(1H, td J 10.9 Hz and 2.1 Hz), 4.36(1H, d J 2.8 Hz), 4.88(1H, q J 6.7 Hz), 7.00(2H, apparent t J 8.8 Hz), 7.21(2H, s), 7.22–7.3(2H, m), 7.62(1H, s). MS m/z 506 (M+H).

EXAMPLE 13

(2R,3S,4S,8R,10R or S) 2-(1-(1-(3,5-Bis(trifluoromethyl)phenyl)ethyl)oxy)-3-(4-fluorophenyl)-4-(piperidin-2-yl)-3,4,5,6-tetrahydropyran (isomer 1); and

EXAMPLE 14

(2R,3S,4S,8R,10S or R) 2-(1-(1-(3,5-Bis(trifluoromethyl)phenyl)ethyl)oxy)-3-(4-fluorophenyl)-4-(piperidin-2-yl)-3,4,5,6-tetrahydropyran (isomer 2)

A mixture of epimeric 2R,3S,4S,8R,10R and 10S) 2-(1-(1-(3,5-bis(trifluoromethyl)phenyl)ethyl)oxy)-3-(4-fluorophenyl)-4-((1-(N-benzylamino)but-3-enyl)-3,4,5,6-tetrahydropyrans (Description 4) was N-allylated (by a procedure analogous to that described in Description 5) and cyclized with Grubbs' catalyst (by a procedure analogous to that described in Example 1) to give the (2R,3S,4S,8R,10R/S) 2-(1-(1-(3,5-bis(trifluoromethyl)-phenyl)ethyl)oxy)-3-(4-fluorophenyl)-4-(N-benzyl-1,2,3,6-tetrahydropyridin-2-yl)-3,4,5,6-tetrahydropyran as a mixture which was separated chromatographically.

Isomer 1:— ¹H NMR (360 MHz, CDCl₃) δ 1.44(3H, d J 6.7 Hz), 1.61(2H, v broad s), 1.73(1H, qd J 13.0 Hz and 5.2 Hz), 2.27(1H broad d J 14.3 Hz), 2.55(1H, m), 2.64(1H, dd J 13.9 Hz and 7.0 Hz), 2.87(1H, dd J 11.6 Hz and 3.5 Hz),2.93(1H, d J 18 Hz), 3.08(1H, d 18 Hz), 3.49(1H, d J 13.6 Hz), 3.64(1H, d J 13.7 Hz), 3.75(1H, ddd J 11.2 Hz, 4.8 Hz and 1.8 Hz), 3.97(1H, td J 10.8 Hz and 2.1 Hz), 4.34(1H, d J 3.2 Hz), 4.86(1H,q J 6.7 Hz), 5.47(1H, d J 10.2 Hz), 5.58(1H, d J 10.2 Hz), 6.97(2H, apparent t J 8.8 Hz), 7.18(2H, s), 7.21–7.30(7H, m), 7.62(1H, s).

Isomer 2:— ¹H NMR (360 MHz, CDCl₃) δ 1 46(3H, d J 6.7 Hz), 1.73–1.90(2H, m), 1.95(1H, broad d J 13.0 Hz), 2.16(1H, m), 2.36(1H, m), 2.54(1H, broad d J 16.9 Hz), 2.80(1H, dd J 11.9 Hz and 3.2 Hz), 3.09(1H, m+d J 12.6 Hz), 3.18(1H, tm J 12.3 Hz), 3.77(1H, dd J 11.3 Hz and 3.2 Hz), 3.97)1H, td J 12.3 Hz and 2.1 Hz), 4.31(1H, d J 13.0 Hz), 4.38(1H, d J 3.1 Hz), 4.88(1H, q J 6.3 Hz), 5.45(1H,broad d J 9.9 Hz), 5.60(1H, broad d J 9.5 Hz),7.0(2H, apparent t 8.8 Hz), 7.19(2H, s), 7.20–7.40(7H, m), 7.62(1H, s).

(2R,3S,4S,8R,10R/S) 2-(1-(1-(3,5-Bis(trifluoromethyl) phenyl)ethyl)oxy)-3-(4-fluorophenyl)-4-(N-benzyl-1,2,3,6-tetrahydropyridin-2-yl)-3,4,5,6-tetrahydropyran (isomer1) was hydrogenated by a procedure analogous to that described in Example 3 to give (2R,3S,4S,8R,10R/S) 2-(1-(1-(3,5-bis(trifluoromethyl)phenyl)ethyl)oxy)-3-(4-fluorophenyl)-4-(piperidin-2-yl)-3,4,5,6-tetrahydropyran (Example 13): ¹H NMR (400 MHz, CDCl₃) δ 1 20–1.27(2H, m), 1.30–1.41(3H, m), 1.46(3H, d J 6.3 Hz), 1.47–1.85(3H, m), 2.19(1H, dd J 12.3 Hz and 2.8 Hz), 2.25(1H, dm J 10.6 Hz),2.39(1H, tm J 11.9 Hz), 2.93(2H tm J 13.7 Hz), 3.77 (1H, dm J 9.8 Hz), 4.00(1H, td J 11.0 Hz and 3.2 Hz), 4.41(1H, d J 3.2 Hz),4.88(1H, q J 6.7 Hz),7.77(2H, apparent t J8.8 Hz), 7.22(2H, s), 7.24–7.27(2H, m), 7.62(1H, s).

Hydrochloride salt: MS m/z 520(M+H).

Similarly (2R,3S,4S,8R,10S/R) 2-(1-(1-(3,5-bis(trifluoromethyl)phenyl)ethyl)-oxy)-3-(4-fluorophenyl)-4-(N-benzyl-1,2,3,6-tetrahydropyridin-2-yl)-3,4,5,6-tetrahydropyran (isomer2) was hydrogenated by a procedure analogous to that described in Example 3 to give (2R,3S,4S,8R,10S/R) 2-(1-(1-(3,5-bis(trifluoromethyl)phenyl)ethyl)oxy)-3-(4-fluorophenyl)-4-(piperidin-2-yl)-3,4,5,6-tetrahydropyran (Example 14): 1H NMR (400 MHz, CDCl₃) δ 1 00–1.12(2H m), 1.25–1.38(3H, m), 1.45(3H, d J 6.7 Hz), 1.65–1.73(2H, m), 1.84(1H), broad d J 12.2 Hz), 2.32(1H, broad d J 10.6 Hz), 2.51(1H, td J 12.2 Hz and 2.8 Hz), 2.60(1H, m), 2.75(1H, dd J 12.2 Hz and 3.1 Hz), 4.00(1H, td J 10.9 Hz and 2.8 Hz), 4.38(1H, d J 3.2 Hz), 4.87(1H, q J 6.7 Hz), 7.00(2H, apparent t J 8.8 Hz), 7.20(2H, s), 7.22–7.25(2H, m), 7.62 (1H, s). MS m/z 520(M+H).

EXAMPLE 15

(2R,3R,4R,8R,10R or 10S) 2-(1-(1-(3,5-Bis(trifluoromethyl)phenyl)-ethyl)oxy)-3-(4-fluorophenyl)-4-(N-benzyl-4-hydroxy-piperidin-2-yl)-3,4,5,6-tetrahydropyran A solution of a mixture of C10 epimeric (2R,3R,4R,8R, 10R and 10S) 2-(1-(1-(3,5-bis(trifluoromethyl)phenyl) ethyl)oxy)-3-(4-fluorophenyl)-4-(N-benzyl-4oxo-1,2,3,4-tetrahydropyridin-2-yl)-3,4,5,6-tetrahydropyran (Description 6, 206 mg, 0.331 mmol) in tetrahydrofuran (3 ml) was cooled to −78° C. Lithium tri-sec-butylborohydride (0.50 ml, 1M solution in tetrahydrofuran, 0.50 mmol) was added dropwise and stirring continued at this temperature for 1 hour. The solution was warmed to room temperature over 30 minutes then sodium borohydride (25.0 mg, 0.662 mmol) in ethanol (2 ml) was added and stirring continued for a further 16 hours. The reaction was quenched with water (0.5 ml) before addition of ethanol (1.4 ml) and potassium hydroxide (24.1 mg, 0.430 mmol). This mixture was then cooled to 0° C. and treated with hydrogen peroxide (167 μl, 1.5 mmol, 27% w/w in water) then allowed to warm to room temperature and stirred for 3 hours. The mixture was concentrated in vacuo and the residue dissolved in diethyl ether (20 ml), washed with water (10 ml) and saturated brine (2×10 ml). The organic phase was dried ($MgSO_4$) and the solvent was removed in vacuo to give the crude product (152 mg). This material was chromatographed on silica, eluting with 2–5% methanol in dichloromethane to give mixture of epimeric alcohols (126 mg, 61%).

A portion (17.0 mg) was purified by preparative t.l.c., eluting with dichloromethane/methanol/ammonia (90:8:1) to give the more polar isomer of the title compound (5.6 mg, 33%). $^1$H NMR (360 MHz, $CDCl_3$), 1.34 (3H, d, J=6.6 Hz), 1.41–1.72 (5H, br), 1.82–1.98 (3H, m), 2.11–2.13 (1H, br), 2.68–2.71 (1H, m), 2.91–2.96 (2H, m), 3.41–3.47 (1H, m), 3.50–3.57 (1H, m), 4.10 (1H, d, J=7.7 Hz), 4.17–4.23 (2H, m), 4.91 (1H, q, J=6.7 Hz), 6.95 (2H, t, J=8.6 Hz), 7.02–7.06 (2H, m), 7.18–7.31 (7H, m), 7.67 (1H, s); m.s. ($ES^+$), 626 ($M^+$+H), 368 ($M^+$−257).

EXAMPLE 16

(2R,3R,4R,8R,10R or 10S) 2-(1-(1-(3,5-Bis(trifluoromethyl)phenyl)-ethyl)oxy)-3-(4-fluorophenyl)-4-(cis 4-hydroxy-piperidin-2-yl)-3,4,5,6-tetrahydropyran (isomer 1); and

EXAMPLE 17

(2R,3R,4R,8R,10R or 10S) 2-(1-(1-(3,5-Bis(trifluoromethyl)phenyl)-ethyl)oxy)-3-(4-fluorophenyl)-4-(trans 4-hydroxy-piperidin-2-yl)-3,4,5,6-tetrahydropyran (isomer 2)

(2R,3R,4R,8R,10R or 10S) 2-(1-(1-(3,5-bis(trifluoromethyl)phenyl)ethyl)oxy)-3-(4-fluorophenyl)-4-(N-benzyl-4-hydroxy-piperidin-2-yl)-3,4,5,6-tetrahydropyran (Example 15, 107 mg, 0.172 mmol, ~1:1 mixture of C4' isomers) in ethanol (9 ml) were treated with ethereal hydrochloric acid (1M, 515 μl, 0.515 mmol) and then 10% palladium on carbon (15 mg). The mixture was shaken under an atmosphere of hydrogen at 48 psi for 1.5 hours. The catalyst was removed by filtration through Celite™ and filtrate concentrated in vacuo to give crude (107 mg). Crude material was purified by preparative t.l.c., eluting with dichloromethane/methanol/ammonia (90:8:1) to give the two alcohol epimers.

EXAMPLE 16 (isomer 1; cis) (15.4 mg, 17%). $^1$H NMR (360 MHz, $CDCl_3$) δ 1.13–1.29 (2H, m), 1.33 (3H, d, J 6.6 Hz), 1.53–1.57 (1H, m), 1.61–1.68 (2H, m), 1.74–1.78 (1H, m), 1.83–1.91 (1H, m), 2.09 (1H, d, J 11.8 Hz), 2.20 (1H, dt, J 12.7 Hz and J 2.3 Hz), 2.75 (1H, dd, J 11.9 Hz and J 8.4 Hz), 2.97–3.02 (1H, m), 3.30–3.37 (1H, m), 3.57–3.65 (1H, m), 4.11–4.34 (1H, m), 4.33 (1H, d, J 8.4 Hz), 5.00 (1H, q, J 6.6 Hz), 6.93 (2H, t, 8.7 Hz), 7.13–7.17 (2H, m), 7.32 (2H, s), 7.73 (1H, s); MS m/z ($ES^+$), 536 ($M^+$+H), 278 ($M^+$−257).

EXAMPLE 17 (isomer 2; trans) (12.4 mg, 13%). $^1$H NMR (360 MHz, $CDCl_3$) δ 1.33 (3H, d, J 6.6 Hz), 1.51–1.69 (6H, m), 1.74–1.82 (1H, m), 2.63–2.78 (4H, m), 3.56–3.63 (1H, m), 4.01–4.02 (1H, m), 4.09–4.14 (1H, m), 4.32 (1H, d, J 8.4 Hz), 4.99 (1H, q, J 6.6 Hz), 6.92 (2H, t J 8.7 Hz), 7.13–7.17 (2H, m), 7.32 (2H, s), 7.73 (1H, s); ); MS m/z ($ES^+$), 536 ($M^+$+H), 278 ($M^+$−257).

EXAMPLE 18

(2R,3R,4R,8R,10R or 10S) 2-(1-(1-(3,5-Bis(trifluoromethyl)phenyl)-ethyl)oxy)-3-(4-fluorophenyl)-4-(cis 4-hydroxy-N-methyl-piperidin-2-yl)-3,4,5,6-tetrahydropyran (isomer 1)

A solution of (2R,3R,4R,8R,10R or 10S) 2-(1-(1-(3,5-bis (trifluoromethyl)-phenyl)ethyl)oxy)-3-(4-fluorophenyl)-4-((cis 4-hydroxy-piperidin-2-yl)-3,4,5,6-tetrahydropyran (Example 16 (isomer 1); 21.0 mg, 0.036 mmol) in dichloroethane (2 ml) was treated with formaldehyde (284 μl, 3.6 mmol, 38% aqueous solution) then sodium triacetoxyborohydride (68.7 mg, 0.324 mmol). After stirring at room temperature for 16 hours, reaction mixture was concentrated in vacuo and the residue partitioned between dichloromethane (3 ml) and saturated aqueous sodium hydrogen carbonate (3 ml). The organic phases were separated on a Bond-Elut™ cartridge, then purified on an SCX cartridge. The solvent was removed in vacuo to give the title compound (12 mg, 62%). $^1$H NMR (360 MHz, $CD_3OD$) δ 1.33 (3H, d, J 6.6 Hz), 1.36–1.54 (3H, m), 1.68–1.79 (4H, m), 1.93–2.03 (2H, m), 2.32 (3H, s), 2.71–2.74 (1H, m), 2.89 (1H, dd, J 12.3 Hz and J 8.0 Hz), 3.22–3.31 (1H, m), 3.59–3.66 (1H, m), 4.14–4.18 (1H, m), 4.22 (1H, d, J 8.0 Hz), 5.00 (1H, q, J 6.6 Hz), 6.95 (2H, t, 8.7 Hz), 7.09–7.13 (2H, m), 7.31 (2H, s), 7.72 (1H, s); MS m/z. ($ES^+$), 550 ($M^+$+H), 292 ($M^+$−257).

EXAMPLE 19

(2R,3R,4R,8R,10R or 10S) 2-(1-(1-(3,5-Bis(trifluoromethyl)phenyl)-ethyl)oxy)-3-(4-fluorophenyl)-4-(trans 4-hydroxy-N-methyl-piperidin-2-yl)-3,4,5,6-tetrahydropyran (isomer 2)

The title compound was prepared using as starting material Example 17 (isomer 2; 2',4'-trans) by a procedure analogous to that described in Example 18. $^1$H NMR (360 MHz, $CD_3OD$) δ 1.33 (3H, d, J 6.6 Hz), 1.47–1.51 (1H, m), 1.61–1.80 (4H, m), 1.87–1.95 (1H, m), 2.25–2.30 (1H, m), 2.37 (3H, s), 2.40–2.51 (1H, m), 2.90 (1H, dd, J 12.1 Hz and J 8.1 Hz), 3.30–3.31 (2H, m), 3.57–3.64 (1H, m), 3.87 (1H, s), 4.09–4.20 (2H, m), 4.99 (1H, q, J 6.6 Hz), 6.94 (2H, t, 8.7 Hz), 7.08–7.11 (2H, m), 7.30 (2H, s), 7.72 (1H, s). MS m/z ($ES^+$), 550 ($M^+$+H), 292 ($M^+$−257).

EXAMPLE 20

(2R,3R,4R,8R,10R or 10S) 2-(1-(1-(3,5-Bis(trifluoromethyl)phenyl)-ethyl)oxy)-3-(4-fluorophenyl)-4-(cis 4-hydroxy-N-ethyl-piperidin-2-yl)-3,4,5,6-tetrahydropyran (isomer 1)

The title compound was prepared by an analogous method to that described in Example 18 except that acetaldehyde was used in the reductive alkylation. MS m/z 564 (M+H).

EXAMPLE 21

(2R,3R,4R,8R,10R or 10S) 2-(1-(1-(3,5-Bis(trifluoromethyl)phenyl)-ethyl)oxy)-3-(4-fluorophenyl)-4-(cis 4-methoxy-piperidin-2-yl)-3,4,5,6-tetrahydropyran a) (2R,3R,4R,8R,10R or 10S) 2-(1-(1-(3,5-Bis(trifluoromethyl)phenyl)ethyl)-oxy)-3-(4-fluorophenyl)-4-(cis 4-hydroxy-piperidin-2-yl)-3,4,5,6-tetrahydropyran (Example 16; 0.23 g, 0.43 mmol) in dichloromethane (3 ml) was treated with 10% aqueous sodium carbonate (3 ml) and then benzyl chloroformate (73 µl). The solution was stirred for 16 hours at room temperature. The layers were separated and the aqueous was dichloromethane extracted (2×10 ml). The organic layer was then dried (MgSO$_4$) and evaporated to give (2R,3R,4R,8R,10R or 10S) 2-(1-(1-(3,5-bis(trifluoromethyl)phenyl)ethyl)oxy)-3-(4-fluorophenyl)-4-(cis N-benzyloxycarbonyl-4-hydroxy-piperidin-2-yl)-3,4,5,6-tetrahydropyran (289 mg): $^1$H NMR (360 MHz, CDCl$_3$) δ 1.35–1.54 (2H, m), 1.55 (3H, d J 5.0 Hz), 1.56–1.80 (3H, m), 2.54 (1H, m), 2.75 (1H, m), 2.90 (1H, m), 3.50 (1H, m), 3.80–4.13 (3H, m), 4.30–4.38 (2H, m), 4.86–4.91 (1H, m), 5.12 (2H, 8), 6.90 (2H, m), 7.15 (2H, m), 7.33 (7H, s), 7.69 (1H, s).

b) The product of step (a) (0.06 g) in dimethylformamide (2 ml) was treated with 60% sodium hydride in mineral oil (7 mg) and the solution was stirred at room temperature for 2 hours before adding methyl iodide (20 µl). The solution was stirred for 72 hours at room temperature before adding water (10 ml) and ethyl acetate (10 ml). The layers were separated and the aqueous was ethyl acetate extracted (2×10 ml). The organic layer was then dried (MgSO$^4$) and evaporated to give (2R,3R,4R,8R,10R or 10S) 2-(1-(1-(3,5-bis (trifluoromethyl)phenyl)ethyl)oxy)-3-(4-fluorophenyl)-4-(cis N-benzyloxycarbonyl-4-methoxy-piperidin-2-yl)-3,4,5, 6-tetrahydropyran (50 mg): $^1$H NMR (360 MHz, CDCl$_3$) δ 1.23–1.73 (8H, m), 2.45 (1H, m), 2.60 (1H, m), 2.72–2.80 (2H, m), 2.83 (1H, m), 3.25 (3H, s), 3.25–3.54 (2H, m), 3.75–4.13 (2H, m), 4.13–4.36 (2H, m), 4.86 (1H, m), 5.12 (2H, s), 6.89 (2H, m), 7.17 (2H, m), 7.31–7.37 (7H, s), 7.70 (1H, s).

c) A solution of the product of step (b) (43.0 mg, 0.063 mmol) in ethanol (4 ml) with 10% palladium on carbon (20 mg) was shaken under an atmosphere of hydrogen at 40 psi for 3 hours. The reaction mixture was then filtered through Celite™ and evaporated in vacuo to give the crude product (33 mg). This was purified by preparative thin layer chromatography, eluting with dichloromethane/methanol/ammonia (90:8:1) to give the title compound (10 mg, 29%). $^1$H NMR (360 MHz, CD$_3$OD) δ 1.06–1.18 (2H, m), 1.33 (3H, d, J 6.6 Hz), 1.61–1.69 (3H, m), 1.84–1.90 (2H, m), 2.08–2.11 (1H, m), 2.18–2.25 (1H, m), 2.75 (1H, dd, J 11.7 Hz and J 8.5 Hz), 2.97–3.04 (2H, m), 3.24 (3H, s), 3.57–3.64 (1H, m), 4.09–4.15 (1H, m), 4.33 (1H, d, J 8.4 Hz), 5.00 (1H, q, J 6.6 Hz), 6.94 (2H, t, 8.7 Hz), 7.13–7.17 (2H, m), 7.32 (2H, s), 7.73 (1H, s). MS m/z. (ES$^+$), 550 (M$^+$+H), 292 (M$^+$–257).

EXAMPLE 22

(2R,3R,4R,8R,10R or 10S) 2-(1-(1-(3,5-Bis(trifluoromethyl)phenyl)-ethyl)oxy)-3-(4-fluorophenyl)-4-(cis 4-methoxy-N-methyl-piperidin-2-yl)-3,4,5,6-tetrahydropyran (2R ,3R,4R,8R,10R or 10S) 2-(1-(1-(3,5-Bis(trifluoromethyl)phenyl)ethyl)oxy)-3-(4-fluorophenyl)-4-(cis 4-hydroxy-N-methyl-piperidin-2-yl)-3,4,5,6-tetrahydropyran hydrochloride (Example 18; 52.0 mg, 0.089 mmol) in N,N-dimethylformamide (3 ml) was treated with sodium hydride (10.7 mg, 60% w/w in mineral oil, 0.267 mmol). After stirring at room temperature for 30 minutes, methyl iodide (5.6 µl, 0.089 mmol) was added and the mixture stirred for a further 64 hours. A further portion of methyl iodide (5.6 µl, 0.089 mmol) was added and the mixture stirred for 3 hours, followed by further portions of methyl iodide (5.6 µl, 0.089 mmol) and sodium hydride (3.0 mg, 60% w/w in mineral oil, 0.089 mmol). After stirring for another 16 hours, reaction was quenched with water (40 ml) and aqueous extracted with diethyl ether (3×40 ml). The combined organic phases were washed with saturated brine (100 ml), dried (MgSO$_4$) and concentrated in vacuo to give the crude product (78 mg). This was purified by preparative t.l.c., eluting with dichloromethane/methanol/ammonia (90:8:1), followed by purification through an SCX cartridge, to give the title compound (2 mg, 4%). $^1$H NMR (360 MHz, CD$_3$OD) δ 1.33 (3H, d, J=6.6 Hz), 1.63–1.67 (1H, m), 1.72–1.78 (2H, m), 1.83–1.86 (2H, m), 1.99–2.07 (2H, m), 2.36 (3H, s), 2.76–2.81 (1H, m), 2.86–2.99 (4H, m), 3.23 (3H, s), 3.59–3.66 (1H, m), 4.14–4.19 (1H, m), 4.22 (1H, d, J=8.0 Hz), 4.99 (1H, q, J=6.6 Hz), 6.96 (2H, t, J=8.7 Hz), 7.07–7.14 (2H, m), 7.31 (2H, s), 7.73 (1H, s); m.s. (ES$^+$), 564 (M$^+$+H), 306 (M$^+$–257).

EXAMPLE 23

(2R,3R,4R,8R,10R or 10S) 2-(1-(1-(3,5-Bis(trifluoromethyl)phenyl)-ethyl)oxy)-3-(4-fluorophenyl)-4-(4-hydroxy-4-methyl-1-piperidin-2-yl)-3,4,5,6-tetrahydropyran a) (2R,3R,4R,8R,10R or 10S) 2-(1-(1-(3,5-Bis(trifluoromethyl)phenyl)-ethyl)oxy)-3-(4-fluorophenyl)-4-(cis N-benzyloxycarbonyl-4-hydroxy-piperidin-2-yl)-3,4,5,6-tetrahydropyran (Example 21a, 0.23 g, 0.34 mmol) in dichloromethane (3 ml) was dissolved in dichloromethane (80 ml), treated with 1,1,1-triacetoxy-1,1-dihydro-1,2-benziodoxol-3(1H)-one (Dess-Martin periodinane) (218 mg) and stirred at 25° C. for 2 hours. The solution was treated with saturated aqueous sodium bisulphite (10 ml), followed after 15 minutes by saturated aqueous sodium bicarbonate (10 ml). The mixture was separated and the aqueous was washed with dichloromethane (2×50 ml). The organic layers were dried (MgSO$_4$) and evaporated to give (2R,3R,4R,8R, 10R or 10S) 2-(1-(1-(3,5-bis(trifluoromethyl)phenyl)ethyl) oxy)-3-(4-fluorophenyl)-4-(N-benzyloxycarbonyl-4-ketopiperidin-2-yl)-3,4,5,6-tetrahydropyran: $^1$H NMR (360 MHz, CDCl$_3$) δ 1.55–1.69 (5H, m), 2.24 (1H, m), 2.42 (3H, m), 2.72 (1H, m), 3.60 (1H, m), 3.95–4.18 (2H, m), 4.22 (1H, d J 5.8 Hz), 4.60 (1H, m), 4.85–4.90 (1H, m), 5.14 (2H, m), 6.89 (2H, m), 7.15 (2H, m), 7.26–7.35 (7H, s), 7.69 (1H, s).

b) The product of step (a) (114 mg, 0.171 mmol) in tetrahydrofuran (5 ml) was added to methyl magnesium bromide (1.47 ml, 3M solution in diethyl ether, 4.41 mmol) in tetrahydrofuran (5 ml) at 0° C. The reaction was warmed to room temperature and stirred for 16 hours. The solvent was removed in vacuo, and the residue partitioned between water (40 ml) and ethyl acetate (40 ml). The aqueous layer was separated and extracted with ethyl acetate (2×40 ml). The combined organics were washed with sodium hydrogen carbonate (50% aq., 2×100 ml), dried (MgSO$_4$) and evaporated in vacuo to give crude material (100 mg) which was chromatographed on silica, eluting with 15–20% ethyl acetate in hexanes to give (2R,3R,4R,8R,10R or 10S) 2-(1-(1-(3,5-bis(trifluoromethyl)-phenyl)ethyl)oxy)-3-(4-fluorophenyl)-4-(N-benzyloxycarbonyl-4-hydroxy-4-methyl-piperidin-2-yl)-3,4,5,6-tetrahydropyran: (53 mg, 64%). 1H NMR (360 MHz, CD$_3$OD) δ 1.03 (3H, s) 1.22–1.54 (8H, m), 1.68–1.71 (1H, m), 2.55–2.65 (1H, br), 2.68–2.76 (1H, br), 3.01 (1H, dt, J=12.7 Hz and J=3.5 Hz), 3.45–3.55 (1H, br),3.88–3.91 (1H, m), 3.98–4.10 (1H, br), 4.29–4.31 (1H, m), 4.42 (1H, d, J=6.0 Hz), 4.90 –5.00 (1H, m), 5.13 (2H, s), 6.86–6.90 (2H, m) 7.05–7.30 (2H, br), 7.28–7.42 (5H, br), 7.48 (2H, s), 7.77 (1H, s).

c) The product of step (b) (53 mg, 0.077 mmol) in ethanol (4 ml) with 10% palladium on carbon (35 mg) was shaken under an atmosphere of hydrogen at 50 psi for 16 hours. The reaction mixture was filtered through Celite™ and concentrated in vacuo to give crude material (49 mg) which was purified by preparative t.l.c., eluting with dichloromethane/methanol/ammonia (90:8:1) to give the title compound (29 mg, 69%). $^1$H NMR (360 MHz, CD$_3$OD) δ 0.91 (3H, s), 1.23–1.29 (1H, m), 1.33 (3H, d, J 6.6 Hz), 1.37–1.50 (3H, m), 1.60–1.64 (2H, m), 1.80–1.89 (1H, m), 2.16–2.30 (2H, m), 2.73–2.79 (1H, m), 2.93–2.97 (1H, m) 3.57–3.64 (1H, m), 4.11–4.15 (1H, m), 4.33 (1H, d, J 8.4 Hz), 5.00 (1H, q, J 6.6 Hz), 6.95 (2H, t, 8.7 Hz), 7.14–7.18 (2H, m), 7.32 (2H, s), 7.73 (1H, s). MS m/z (ES$^+$), 550 (M$^+$+H), 292 (M$^+$–257).

EXAMPLE 24

(2R,3R,4R,8R,10R or 10S) 2-(1-(1-(3,5-Bis(trifluoromethyl)phenyl)-ethyl)oxy)-3-(4-fluorophenyl)-4-(4-keto-piperidin-2-yl)-3,4,5,6-tetrahydropyran (2R,3R,4R,8R,10R or 10S) 2-(1-(1-(3,5-Bis(trifluoromethyl)phenyl)ethyl)oxy)-3-(4-fluorophenyl)-4-(N-benzyloxycarbonyl-4-keto-piperidin-2-yl)-3,4,5,6-tetrahydropyran (Example 23a; 36.0 mg, 0.054 mmol) in ethanol (4 ml) with 10% palladium on carbon (20 mg) was shaken under an atmosphere of hydrogen at 35 psi for 2 hours. The reaction mixture was then filtered through Celite™ and evaporated in vacuo to give the crude product (35 mg). A portion (17 mg) was purified by preparative t.l.c., eluting with dichloromethane/methanol/ammonia (90:8:1) to give the title compound (7.0 mg, 41%). $^1$H NMR (360 MHz, CD$_3$OD) δ 1.34 (3H, d, J 6.3 Hz), 1.56–1.69 (2H, m), 1.79–1.94 (2H, m), 2.10–2.14 (1H, m), 2.28–2.44 (3H, m), 2.84–2.90 (1H, m), 3.59–3.65 (2H, m), 4.14–4.17 (1H, m), 4.30–4.37 (1H, m), 4.75–4.93 (1H, br), 5.01 (1H, q, J 6.6 Hz), 6.93 (2H, t, J 8.9 Hz), 7.11–7.15 (2H, m), 7.33 (2H, s), 7.73 (1H, s). MS m/z (ES$^+$), 276 (M$^+$–257).

EXAMPLE 25

(2R,3R,4R,8R,10R)-2-(1-(1-(3,5-Bis(trifluoromethyl)phenyl)ethyl)oxy)-3-(4-fluorophenyl)-4-(N-methyl-2-morpholinyl)-3,4,5,6-tetrahydropyran; and (2R,3R,4R,8R,10S)-2-(1-(1-(3,5-Bis(trifluoromethyl)phenyl)ethyl)oxy)-3-(4-fluorophenyl)-4-(N-methyl-2-morpholinyl)-3,4,5,6-tetrahydropyran a) A solution of (2R,3R,4S,8R)-2-(1-(1-(3,5-Bis(trifluoromethyl)phenyl)ethyl)-oxy)-3-(4-fluorophenyl)-4-vinyl-3,4,5,6-tetrahydropyran (isomer 4, Description 1; 1.17 g, 2.5 mmol) and 50% m-chloroperbenzoic acid (1.75 g, 5.0 mol) in dichloromethane (75 ml) was stirred at 25° C. for 16 hours. The solution was filtered, and washed with saturated aqueous sodium bisulphite (25 ml), saturated aqueous sodium bicarbonate (25 ml) and brine (25 ml). The solution was then dried (MgSO$_4$) and evaporated to give (2R,3R,4R, 8R,10R and 10S)-2-(1-(1-(3,5-bis(trifluoromethyl)phenyl) ethyl)oxy)-3-(4-fluorophenyl)-4-oxiranyl-3,4,5,6-tetrahydropyran (1.2 g): $^1$H NMR (360 MHz, CDCl$_3$) δ 1.37(3H, d J 5.0 Hz), 1.48–1.64 (3H, m), 1.70 (1H, dt J 11.8 Hz and 4.7 Hz), 1.82 (1H, m), 1.98 (1H, dd J 4.7 Hz and 2.5 Hz), 2.36–2.62 (2H, m), 2.65 (1H, dd J 11.2 Hz and 9.7 Hz), 3.52 (1H, dt J 9.0 Hz and 2.5 Hz), 4.16 (1H, m) 4.21 (1H, d J 8.6 Hz), 4.96 (1H, q J 6.5 Hz), 6.91–7.00 (4H, m), 7.20 (2H, s), 7.68 (1H, s).

b) A solution of the product of step (a) (0.37 g, 0.77 mmol) in tetrahydrofuran (75 ml) was added to a premixed solution of allyl alcohol (10 ml) and sodium hydride (300 mg) in tetrahydrofuran (5 ml) and stirred at 80° C. for 72 hours. The solution was cooled to room temperature and azeotroped once with toluene. The residue was partitioned between saturated aqueous sodium bicarbonate (75 ml) and ethyl acetate (75 ml). The mixture was separated and the organics were washed with brine (25 ml). The solution was then dried (MgSO$_4$) and evaporated. The residue was dissolved in dichloromethane (80 ml), treated with Dess-Martin periodinane (656 mg) and stirred at 25° C. for 16 hours. The solution was treated with saturated aqueous sodium bisulphite (25 ml), followed after 15 minutes by saturated aqueous sodium bicarbonate (25 ml). The mixture was separated and the aqueous was washed with dichloromethane (2×50 ml). The organic layers were dried (MgSO$_4$) and evaporated and the residue purified by column chromatography on silica gel (eluting with 20% ethyl acetate in isohexane), to give the (2R,3R,4R,8R)-2-(1-(1-(3,5-bis(trifluoromethyl)phenyl) ethyl)oxy)-3-(4-fluorophenyl)-4-(allyloxyacetyl)-3,4,5,6-tetrahydropyran (0.286 g): $^1$H NMR (360 MHz, CDCl$_3$) δ 1.37(3H, d J 5.7 Hz), 1.72–1.89 (2H, m), 3.05 (1H, dd J 11.5 Hz and 8.3 Hz), 3.05 (1H, dd J 10.8 Hz and 4.3 Hz), 3.59 (1H, td J 11.5 Hz and 3.2 Hz), 3.64 (1H, s), 3.68 (1H, s), 3.74 (1H, dd J 12.6 Hz and 5.8 Hz), 3.82 (1H, dd J 12.9 Hz and 5.8 Hz), 4.17 (1H, m), 4.25 (1H, d J 9.0 Hz), 4.97 (1H, q J 6.5 Hz), 5.10–5.15 (2H, m), 5.75 (1H, m), 6.92 (2H, m), 7.03 (2H, m), 7.22 (2H, s), 7.69 (1H, s).

c) A solution of the product of step (b) (0.29 g, 0.53 mmol) in dichloromethane:methanol (1:1) (20 ml) was cooled –78° C. and flushed with oyxgen then with ozone until a blue coloration of the solvent persisted. The solution was then purged with oxygen and treated with dimethylsulphide (280 μl) before being allowed to warm to room temperature over 16 hours. The solution was treated with 2.0M methylamine in tetrahydrofuran (2 ml) and then sodium cyanoborohydride (101 mg). Sufficient acetic acid was then added to bring the solution to pH 5 and the solution was stirred for 16 hours at room temperature. The solvent was evaporated and the residue was partitioned between saturated aqueous sodium bicarbonate (75 ml) and dichloromethane (75 ml). The organic layer was then dried (MgSO$_4$) and evaporated and the residue purified by column chromatography on silica gel (eluting with 8% methanol in dichloromethane, 1% ammonia). The isomers were separated by preparative HPLC to give the title compounds.

Isomer 1: $^1$H NMR (360 MHz, CD$_3$OD) δ 1.57 (3H, d J 4.0 Hz), 1.40 (1H, m), 1.50–1.62 (3H, m), 1.83 (1H, dt J 11.8 Hz and 3.2 Hz), 2.01 (3H, s), 2.32 (1H, d J 12.2 Hz), 2.63

(1H, dd J 11.8 Hz and 8.3 Hz), 2.99–3.09 (2H, m), 3.16 (1H, t J 11.5 Hz), 3.36 (2H, m), 3.90 (1H, dd J 11.2 Hz and 4.0 Hz), 3.97 (1H, d J 7.9 Hz), 4.75 (1H, q J 6.4 Hz), 6.73 (2H, m), 6.86 (2H, m), 7.07 (2H, s), 7.49 (1H, s).

Isomer 2: $^1$H NMR (360 MHz, CD$_3$OD) δ 1.37 (3H, d J 6.8 Hz), 1.50 (1H, m), 1.63 (1H, dt J 10.4 Hz and 2.9 Hz), 1.78 (1H, m), 2.04 (1H, dt J 11.8 Hz and 3.6 Hz), 2.11 (3H,s), 2.45–2.61 (3H, m), 3.40 (1H, t J 10.8 Hz), 3.50 (1H, t J 11.5 Hz and 2.2 Hz), 3.56–3.64 (2H, m), 3.79 (1H, dd J 11.2 Hz and 2.9 Hz), 4.10 (1H, dd J 11.5 Hz and 2.5 Hz), 4.28 (1H, d J=7.6 Hz), 4.99 (1H, q J 6.8 Hz), 6.97 (2H, m), 7.14 (2.2 Hz), 7.30 (2H, s), 7.72 (1H, s).

EXAMPLE 26

(2R,3R,4R,8R,10R and 10S)-2-(1-(1-(3,5-Bis(trifluoromethyl)phenyl)-ethyl)oxy)-3-(4-fluorophenyl)-4-(N-methyl-3-morpholinyl)-3,4,5,6-tetrahydropyran a) (2R,3R,4R,8R,10R and 10S)-2-(1-(1-(3,5-Bis(trifluoromethyl)phenyl)-ethyl)oxy)-3-(4-fluorophenyl)-4-oxiranyl-3,4,5,6-tetrahydropyran (Example 25a; 0.50 g, 1.05 mmol) in methanol (30 ml) was treated with N-methylaminoethanol (83.8 μl, 1.05 mmol) and the mixture heated to reflux. After 48 hours, a further portion of N-methylaminoethanol (41.8 μl, 0.523 mmol) was added and refluxing continued for a further 2 hours after which time N-methylaminoethanol (41.8 μl, 0.523 mmol) was again added. After refluxing for 16 hours, reaction mixture was concentrated in vacuo to give a yellow oil (651 mg). This oil was chromatographed on silica, eluting with 100% dichloromethane, then dichloromethane/methanol/ammonia (90:8:1) giving (2R, 3R,4R,8R,10R and 10S)-2-(1-(1-(3,5-bis(trifluoromethyl) phenyl)ethyl)oxy)-3-(4-fluorophenyl)-4-(2-hydroxy-N-methyl-N-(2-hydroxyethyl)-2-ethylamino)-3,4,5,6-tetrahydropyran as a 3:1 mixture of isomers (540 mg, 93%). $^1$H NMR (360 MHz, CD$_3$OD), δ 1.33–1.35 (3H, m), 1.49–1.52 (1H, m), 1.68–1.82 (1H, m), 1.93–1.99 (1H, m), 2.06 (3H, s), 2.13–2.32 (2H, m), 2.35–2.40 (3H, m), 2.80–2.85 (1H, m), 3.50–3.53 (2H, m), 3.58–3.65 (1H, m), 4.09–4.14 (1H, m), 4.29–4.35 (1H, m), 4.99–5.04 (1H, m), 6.90–6.97 (2H, m), 7.11–7.15 (2H, m), [7.32 and 7.33] (2H, s), 7.73 (1H, s); MS m/z (ES$^+$) 576 (M$^+$+Na) 554 (M$^+$+H), 296 (M$^+$−257).

b) The product of step (a) (337 mg, 0.609 mmol) in tetrahydrofuran (75 ml) was treated with triphenylphosphine (240 mg, 0.914 mmol) and diethyl azodicarboxylate (144 μl, 159 mg) then heated to reflux for 24 hours. The solvent was removed in vacuo and the resulting residue partitioned between dichloromethane (80 ml) and sodium hydrogen carbonate (50% aq, 80 ml). The aqueous was extracted with dichloromethane (80 ml) then the combined organics were dried (MgSO$_4$), washed with saturated brine (100 ml) and evaporated to give yellow oil (1.00 g). The crude oil was chromatographed on silica, eluting with dichloromethane/methanol/ammonia (360:8:1) giving material (420 mg) which was chromatographed on silica a second time, eluting with dichloromethane/methanol/ammonia (270:8:1), to give still impure material (400 mg). A portion (300 mg) was purified through an SCX cartridge, followed by preparative t.l.c., eluting with dichloromethane/methanol/ammonia (180:8:1) to give a colourless solid (23 mg). This material was dissolved in ethyl acetate and treated with ethereal hydrochloric acid (1M, 43 μl, 0.043 mmol). The solvent was removed in vacuo and product triturated in ethyl acetate to give the title compounds as a 1:2 mixture of isomers (16 mg, 5%). $^1$H NMR (360 MHz, CD$_3$OD), 1.33–1.35 (3H, m), 1.54–1.66 (1H, m), 1.70–1.80 (1H, m), 1.86–1.96 (1H, m), 2.21–2.37 (2H, m), 2.45 (3H, s), 2.72–2.96 (2H, m), 3.04–3.24 (2H, m), 3.38–3.69 (1H, m), [3.83–3.86 and 3.94–3.98] (1H, m), 4.06–4.15 (2H, br), [4.30–4.32 and 4.39–4.01] (1H, m), 4.99–5.05 (1H, m), 6.93–7.00 (2H, m), [7.08–7.11 and 7.16–7.22](2H, m), 7.31–7.46 (2H, m), 7.74 (1H, s); MS m/z (ES$^+$), 536 (M$^+$+H), 279 (M$^+$−257 +H).

The invention claimed is:
1. A compound of the formula (I):

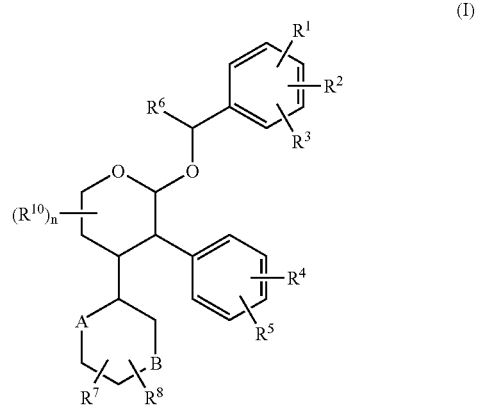

wherein:
A represents NR$^9$ or O;
B represents a bond, CH$_2$, NH, NR$^9$ or O, wherein one or both hydrogen atoms in said CH$^2$ moiety may be replaced with one or both of R$^7$ and R$^8$, or alternatively, one of the hydrogen atoms in said CH$_2$ moiety together with a hydrogen atom from an adjacent carbon are replaced by a double bond;
with the proviso that when A is O, then B is NR$^9$;
R$^1$ is hydrogen, halogen, C$_{1-6}$alkyl, C$_{1-6}$alkoxy, fluoroC$_{1-6}$alkyl, fluoroC$_{1-6}$alkoxy, C$_{3-7}$cycloalkyl, C$_{3-7}$cycloalkylC$_{1-4}$alkyl, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, wherein R$^a$ and R$^b$ each independently represent hydrogen or C$_{1-4}$alkyl;
R$^2$ is hydrogen, halogen, C$_{1-6}$alkyl, fluoroC$_{1-6}$alkyl or C$_{1-6}$alkoxy substituted by C$_{1-4}$alkoxy;
R$^3$ is hydrogen, halogen or fluoroC$_{1-6}$alkyl;
R$^4$ is hydrogen, halogen, C$_{1-6}$alkyl, C$_{1-6}$alkoxy, fluoroC$_{1-6}$alkyl, fluoroC$_{1-6}$alkoxy, hydroxy, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, wherein R$^a$ and R$^b$ are as previously defined;
R$^5$ is hydrogen, halogen, C$_{1-6}$alkyl, fluoroC$_{1-6}$alkyl or C$_{1-6}$alkoxy substituted by C$_{1-4}$alkoxy;
R$^6$ represents hydrogen or a C$_{1-4}$alkyl group optionally substituted by a hydroxy group;
R$^7$ and R$^8$ each independently represent hydrogen, hydroxy, COR$^e$, CO$_2$R$^e$, C$_{1-4}$alkyl optionally substituted by a C$_{1-4}$alkoxy or hydroxyl group, or C$_{1-4}$alkoxy optionally substituted by a C$_{1-4}$alkoxy or hydroxyl group, where R$^e$ is hydrogen, methyl, ethyl or benzyl;
or, when they are attached to the same carbon atom, R$^7$ and R$^8$ may together represent =O, =CHCO$_2$R$^a$, —O(CH₂)ₘO—, —CH₂O(CH₂)ₚ—, —CH₂OCH₂C(O)—, —CH₂OCH₂CH(OH)—, —CH₂OCH₂C(CH₃)₂—, —CH₂OC(CH₃)₂CH₂—, —C(CH₃)₂OCH₂CH₂—, —CH₂C(O)OCH₂—, —OC(O)CH₂CH₂—, —C(O)OCH₂CH₂—, —C(O)OC(CH₃)₂CH₂—, —C(O)OCH₂C(CH₃)₂—, —OCH₂(CH₂)ₚ—, —OC(CH₃)₂CH₂CH₂—, —OCH₂C(CH₃)₂CH₂—, —OCH₂CH₂C(CH₃)₂—, —OCH₂CH=CHCH₂—, —OCH₂CH(OH)CH₂CH₂—, —OCH₂CH₂CH(OH)CH₂—, —OCH₂C(O)CH₂CH₂—, —OCH₂CH₂C(O)CH₂—, or a group of the formula

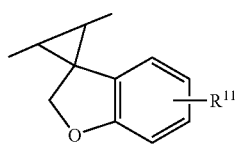

or, where they are attached to adjacent carbon atoms, R⁷ and R⁸ may together represent —OCH₂CH₂— or —OCH₂CH(OH)—, or R⁷ and R⁸ may together form a fused benzene ring;

or, R⁷ and R⁸ together form a C$_{1-2}$alkylene bridge across the pyrrolidine, piperidine, morpholine or piperazine ring to which they are attached;

R⁹ represents benzyl, C$_{1-4}$alkyl, C$_{3-7}$cycloalkyl, C$_{3-7}$cycloalkylC$_{1-4}$alkyl, or C$_{2-4}$alkyl substituted by a C$_{1-4}$alkoxy or hydroxyl group;

R¹⁰ represents halogen, C$_{1-6}$alkyl, CH₂OR$^c$, oxo, CO₂R$^a$ or CONR$^a$R$^b$ where R$^a$ and R$^b$ are as previously defined and R$^c$ represents hydrogen, C$_{1-6}$alkyl or phenyl;

R¹¹ represents hydrogen, halogen, hydroxy, C$_{1-4}$alkyl, hydroxyC$_{1-4}$alkyl or fluoroC$_{1-4}$alkyl;

n is zero, 1 or 2;

m is 1 or 2; and p is 1, 2 or 3;

or a pharmaceutically acceptable salt thereof.

2. The compound of claim 1 wherein R¹ hydrogen, C$_{1-4}$alkyl, C$_{1-4}$alkoxy, halogen or CF₃.

3. The compound of claim 1 wherein R² is hydrogen, C$_{1-4}$alkyl, C$_{1-4}$alkoxy, halogen or CF₃.

4. The compound of claim 1 wherein R³ is hydrogen, fluorine, chlorine or CF₃.

5. The compound of claim 1 wherein R⁴ is hydrogen or fluorine.

6. The compound of claim 1 wherein R⁵ is hydrogen, fluorine, chlorine or CF₃.

7. The compound of claim 1 wherein R⁶ is a methyl or hydroxymethyl group.

8. The compound of claim 1 wherein R⁷ is hydrogen, hydroxy, C$_{1-2}$alkyl substituted by hydroxy, C$_{1-4}$alkoxy or CO²R$^e$(where R$^e$ is hydrogen, methyl ethyl or benzyl).

9. The compound of claim 1 wherein R⁸ is hydrogen or C$_{1-4}$alkyl.

10. The compound of claim 1 wherein R⁷ and R⁸ are attached to the same carbon atom.

11. The compound of claim 1 wherein B represents CH₂, and both hydrogen atoms in said CH₂ moiety are replaced by R⁷ and R⁸ forming a moiety of the formula CR⁷R⁸.

12. The compound of claim 1 wherein n is zero.

13. The compound of claim 1 of the formula (Ia)

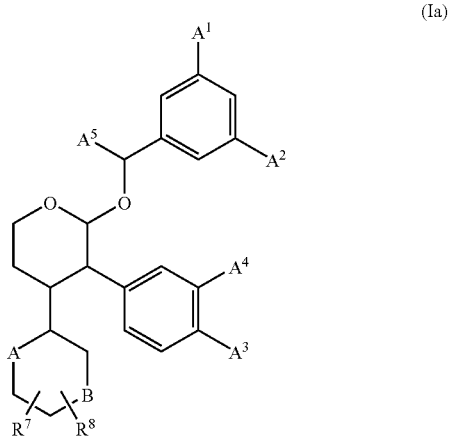

(Ia)

wherein:

A¹ is fluorine or CF₃;

A² is fluorine or CF₃;

A³ is fluorine or hydrogen;

A⁴ is fluorine or hydrogen;

A⁵ is methyl; and or a pharmaceutically acceptable salt thereof.

14. A compound which is selected from the group consisting of:

(2R,3R,4R,8R,10R/S) 2-(1-(1-(3,5-bis(trifluoromethyl)phenyl)ethyl)oxy)-3-(4-fluorophenyl)-4-(N-benzyl-1,2,3,6-tetrahydropyridin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(N-benzylpyrrolidin-2-yl)-3,4,5,6-tetrahydropyran;

(2R,3S,4S,8R,10R or 10S) 2-(1-(1-(3,5-bis(trifluoromethyl)phenyl)ethyl)oxy-3-(4-fluorophenyl)-4-(N-benzylpyrrolidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(N-benzyl-4-hydroxy-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(cis 4-hydroxy-N-methyl-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(trans 4-hydroxy-N-methyl-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(cis 4-hydroxy-N-ethyl-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(cis 4-methoxy-N-methyl-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(4-hydroxy-4-methyl-1-piperidin-2-yl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(4-ketopiperidin-2-yl)-3,4,5,6-tetrahydropyran;

(2R,3R,4R,8R,10R)-2-(1-(1-(3,5-bis(trifluoromethyl)phenyl)ethyl)oxy)-3-(4-fluorophenyl)-4-(N-methyl-2-morpholinyl)-3,4,5,6-tetrahydropyran;

(2R,3R,4R,8R,10S)-2-(1-(1-(3,5-bis(trifluoromethyl)phenyl)ethyl)oxy)-3-(4-fluorophenyl)-4-(N-methyl-2-morpholinyl)-3,4,5,6-tetrahydropyran;

(2R,3R,4R,8R,10R or 10S) 2-(1-(1-(3,5-bis(trifluoromethyl)phenyl)ethyl)oxy)-3-(4-fluorophenyl)-4-(N-methyl-3-morpholinyl)-3,4,5,6-tetrahydropyran;

or a pharmaceutically acceptable salt thereof.

15. A compound of the formula (I):

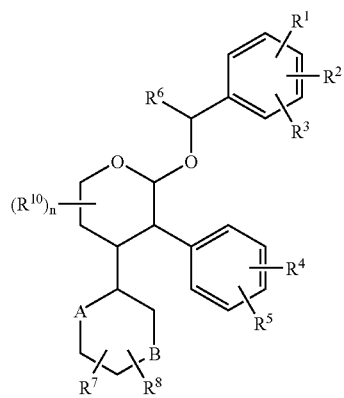

wherein:

A represents $NR^9$ or O;

B represents a bond, $CH_2$, $NR^9$ or O, wherein one or both hydrogen atoms in said $CH_2$ moiety may be replaced with one or both of $R^7$ and $R^8$, or alternatively, one of the hydrogen atoms in said $CH_2$ moiety together with a hydrogen atom from an adjacent carbon are replaced by a double bond;

with the proviso that when A is O, then B is $NR^9$;

$R^1$ is hydrogen, halogen, $C_{1-6}$alkyl, $C_{1-6}$alkoxy, fluoro$C_{1-6}$alkyl, fluoro$C_{1-6}$alkoxy, $C_{3-7}$cycloalkyl, $C_{3-7}$cycloalkyl$C_{1-4}$alkyl, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, fluoro$C_{1-6}$alkyl or $C_{1-6}$alkoxy substituted by $C_{1-4}$alkoxy;

$R^3$ is hydrogen, halogen or fluoro$C_{1-6}$alkyl;

$R^4$ is hydrogen, halogen, $C_{1-6}$alkyl, $C_{1-6}$alkoxy, fluoro$C_{1-6}$alkyl, fluoro$C_{1-6}$alkoxy, fluoro$C_{1-6}$alkoxy, hydroxy, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, fluoro$C_{1-6}$alkyl or $C_{1-6}$alkoxy substituted by $C_{1-4}$alkoxy;

$R^6$ represents hydrogen or a $C_{1-4}$alkyl group optionally substituted by a hydroxy group;

$R^7$ and $R^8$ are attached to the same carbon atom, $R^7$ and $R^8$ together represent =O, =CHCO$_2R^a$, —O(CH$_2$)$_m$O—, —CH$_2$O(CH$_2$)$_p$—, —CH$_2$OCH$_2$C(O)—, —CH$_2$OCH$_2$CH(OH)—, —CH$_2$OCH$_2$C(CH$_3$)$_2$—, —CH$_2$OC(CH$_3$)$_2$CH$_2$—, —C(CH$_3$)$_2$OCH$_2$CH$_2$—, —CH$_2$C(O)OCH$_2$—, —OC(O)CH$_2$CH$_2$—, —C(O)OCH$_2$CH$_2$—, —C(O)OC(CH$_3$)$_2$CH$_2$—, —C(O)OCH$_2$C(CH$_3$)$_p$—, —OC(CH$_3$)$_2$CH$_2$CH$_2$—, —OCH$_2$C(CH$_3$)$_2$CH$_2$—, —OCH$_2$CH$_2$C(CH$_3$)$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, —OCH$_2$CH$_2$C(O)CH$_2$—, or a group of the formula

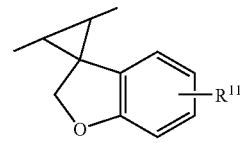

or, where they are attached to adjacent carbon atoms, $R^7$ and $R^8$ may together represent —OCH$_2$CH$_2$— or —OCH$_2$CH(OH)—, or $R^7$ and $R^8$ may together form a fused benzene ring;

or, $R^7$ and $R^8$ together form a $C_{1-2}$alkylene bridge across the pyrrolidine, piperidine, morpholine or piperazine ring to which they are attached;

$R^9$ represents Hydrogen, benzyl, $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;

$R^{10}$ represents halogen, $C_{1-6}$alkyl, $CH_2OR^c$, oxo, $CO_2R^a$ or $CONR^1R^b$ where $R^a$ and $R^b$ are as previously defined and $R^c$ represents hydrogen, $C_{1-6}$alkyl or phenyl;

$R^{11}$ represents hydrogen, halogen, hydroxy, $C_{1-4}$alkyl, hydroxy$C_{1-4}$alkyl or fluoro$C_{1-4}$alkyl;

n is zero, 1 or 2;

m is 1 or 2; and p is 1, 2 or 3;

or a pharmaceutically acceptable salt thereof.

16. The compound of claim 15 of the formula (Ia)

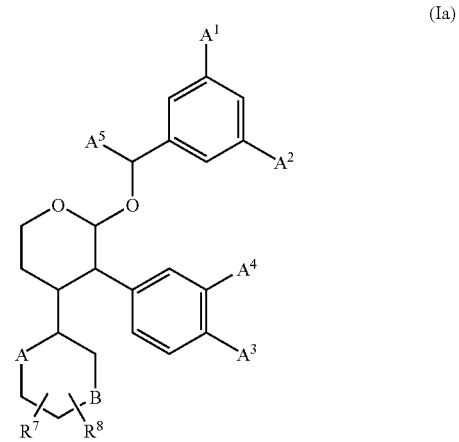

wherein:

$A^1$ is fluorine or $CF_3$;

$A^2$ is fluorine or $CF_3$;

$A^3$ is fluorine or hydrogen;

$A^4$ is fluorine or hydrogen;

$A^5$ methyl; and or a pharmaceutically acceptable salt thereof.

17. A compound which is selected from the group consisting of:
- (2R,3R,4R,8R,10R or 10S) 2-(1-(1-(3,5-bis(trifluoromethyl)phenyl)ethyl)oxy)-3-(4-fluorophenyl)-4-(piperidin-2-yl)-3,4,5,6-tetrahydropyran;
- (2R,3R,4R,8R,10R or 10S) 2-(1-(1-(3,5-bis(trifluoromethyl)phenyl)ethyl)oxy)-3-(4-fluorophenyl)-4-(pyrrolidin-2-yl)-3,4,5,6-tetrahydropyran;
- (2R,3S,4S,8R,10R or 10S) 2-(1-(1-(3,5-bis(trifluoromethyl)phenyl)ethyl)oxy)-3-(4-fluorophenyl)-4-(pyrrolidin-2-yl)-3,4,5,6-tetrahydropyran;
- (2R,3S,4S,8R,10R or 10S) 2-(1-(1-(3,5-bis(trifluoromethyl)phenyl)ethyl)oxy)-3-(4-fluorophenyl)-4-(piperidin-2-yl)-3,4,5,6-tetrahydropyran;
- (2R,3R,4R,8R,10R or 10S) 2-(1-(1-(3,5-bis(trifluoromethyl)phenyl)ethyl)oxy)-3-(4-fluorophenyl)-4-(cis 4-hydroxy-piperidin-2-yl)-3,4,5,6-tetrahydropyran;
- (2R,3R,4R,8R,10R or 10S) 2-(1-(1-(3,5-bis(trifluoromethyl)phenyl)ethyl)oxy)-3-(4-fluorophenyl)-4-(trans 4-hydroxy-piperidin-2-yl)-3,4,5,6-tetrahydropyran; and
- (2R,3R,4R,8R,10R or 10S) 2-(1-(1-(3,5-bis(trifluoromethyl)phenyl)ethyl)oxy)-3-(4-fluorophenyl)-4-(cis 4-methoxy-piperidin-2-yl)-3,4,5,6-tetrahydropyran; and or a pharmaceutically acceptable salt thereof.

18. A pharmaceutical composition comprising a compound of claim 1 and a pharmaceutically acceptable carrier or excipient.

19. A method for the treatment of pain, inflammation, migraine, emesis, postherpetic neuralgia, depression or anxiety, which method comprises administration to a patient in need thereof of a therapeutically effective amount of the compound of claim 1.

20. A method for the prevention of emesis induced by chemotherapy and radiation, which method comprises administration to a patient in need thereof of a therapeutically effective amount of the compound of claim 1.

* * * * *